(12) United States Patent
Cundy et al.

(10) Patent No.: US 11,517,608 B2
(45) Date of Patent: Dec. 6, 2022

(54) PEPTIDE-CONTAINING FORMULATIONS

(71) Applicant: COHBAR, INC., Menlo Park, CA (US)

(72) Inventors: Kenneth Cundy, Atherton, CA (US); Kent K. Grindstaff, San Jose, CA (US); Remi Magnan, Sunnyvale, CA (US)

(73) Assignee: COHBAR, INC., Menlo Park, CA (US)

( * ) Notice: Subject to any disclaimer, the term of this patent is extended or adjusted under 35 U.S.C. 154(b) by 0 days.

(21) Appl. No.: 16/981,870

(22) PCT Filed: Mar. 27, 2019

(86) PCT No.: PCT/US2019/024331
§ 371 (c)(1),
(2) Date: Sep. 17, 2020

(87) PCT Pub. No.: WO2019/191264
PCT Pub. Date: Oct. 3, 2019

(65) Prior Publication Data
US 2021/0030835 A1 Feb. 4, 2021

Related U.S. Application Data

(60) Provisional application No. 62/648,746, filed on Mar. 27, 2018.

(51) Int. Cl.
| | | |
|---|---|---|
| A61K 38/10 | (2006.01) | |
| A61K 9/08 | (2006.01) | |
| A61K 47/18 | (2017.01) | |
| A61K 47/26 | (2006.01) | |

(52) U.S. Cl.
CPC ............. A61K 38/10 (2013.01); A61K 9/08 (2013.01); A61K 47/183 (2013.01); A61K 47/26 (2013.01)

(58) Field of Classification Search
CPC ........ A61K 38/10; A61K 9/08; A61K 47/183; A61K 47/26; A61K 9/0019; A61K 9/19; A61K 35/17; A61K 47/22; C07K 7/08; A61P 1/16; A61P 3/00; A61P 3/04; A61P 35/00
See application file for complete search history.

(56) References Cited

U.S. PATENT DOCUMENTS

| | | | |
|---|---|---|---|
| 7,998,928 B2 | 8/2011 | Cohen et al. | |
| 8,309,525 B2 | 11/2012 | Barzilai et al. | |
| 8,637,470 B2 | 1/2014 | Cohen et al. | |
| 8,653,027 B2 | 2/2014 | Cohen et al. | |
| 10,064,914 B2 | 9/2018 | Cohen et al. | |
| 10,391,143 B2 | 8/2019 | Cohen et al. | |
| 11,111,271 B2 * | 9/2021 | Cundy ................ | C07K 14/47 |
| 2010/0254992 A1 | 10/2010 | Das et al. | |
| 2012/0121633 A1 | 5/2012 | Paul et al. | |
| 2013/0123168 A1 | 5/2013 | Cohen et al. | |
| 2014/0213527 A1 | 7/2014 | Cohen et al. | |
| 2014/0296139 A1 | 10/2014 | Cohen et al. | |
| 2017/0049853 A1 | 2/2017 | Cohen et al. | |

FOREIGN PATENT DOCUMENTS

| | | |
|---|---|---|
| WO | 01/76532 A2 | 10/2001 |
| WO | 2014/144521 A1 | 9/2014 |
| WO | 2018/064098 A1 | 4/2018 |

OTHER PUBLICATIONS

Berge et al, Journal of Pharmaceutical Sciences, Jan. 1977, vol. 66, No. 1, 1-19 (Year: 1977).*
ASHP Handbook on Injectable Drugs, Toissel, 4th ed., pp. 622-630 (1986).
Feng et al., Inhibition of aggregation of physically modified rice proteins by isoconcentration of L-Arg and L-Glu, International Journal of Biological Macromolecules, 127:693-700 (2019).
Fuku et al., The Mitochondrial-Derived Peptide MOTS-c: A Player in Exceptional Longevity?, Aging Cell, 14(6): 921-923 (2015).
International Application No. PCT/US2019/024331, International Preliminary Report on Patentability, dated Oct. 8, 2020.
International Application No. PCT/US2019/024331, International Search Report and Written Opinion, dated Jul. 25, 2019.
Lee et al., Humanin: A Harbinger of Mitochondrial-Derived Peptides?, Trends Endocrinol. Metab., 24(5):222-228 (2013).
Lee et al., MOTS-c: A Novel Mitochondrial-Derived Peptide Regulating Muscle and Fat Metabolism, Free Radic. Biol. Med., 100:182-187 (2016).
Lee et al., The mitochondrial-derived peptide MOTS-c promotes metabolic homeostasis and reduces obesity and insulin resistance, Cell Metab., 21:443-454 (2015).
Pharmaceutics and Pharmacy Practice, J . B . Lippincott Company, Philadelphia, Pa., Banker and Chalmers, eds., pp. 238-250 (1982).
Randolph et al., Surfactant-protein interactions, Pharm. Biotechnol., 13:159-175 (2002).
UniProtKB/Swiss-Prot A0A0C5B5G6.1; 2015; accessed from https://www.ncbi.nlm.nih.gov/protein/A0A0C5B5G6.1?report=genpept (Year: 2015).
Wang, Instability, stabilization, and formulation of liquid protein pharmaceuticals, Int. J. Pharm., 185:129-88 (1999).
Wang, Lyophilization and development of solid protein pharmaceuticals, Int. J. Pharm., 203:1-60 (2000).
Wu et al., Non-alcoholic fatty liver disease incidence, remission and risk factors among a general Chinese population with a 6-year follow-up, Sci. Rep., 8(1):7557 (2018).
Zarse et al., A Mitochondrially Encoded Hormone Ameliorates Obesity and Insulin Resistance, Cell Metab., 21(3):355-356 (2015).
U.S. Appl. No. 17/393,944, filed Nov. 25, 2021 (projected), Cundy et al.

* cited by examiner

Primary Examiner — Sudhakar Katakam
(74) Attorney, Agent, or Firm — Marshall, Gerstein & Borun LLP

(57) ABSTRACT

A formulation comprising glutamic acid, or a salt thereof, and an effective amount of a peptide is provided. The invention also provides a method of preparing the formulation, methods of treating a condition using the formulation, and a kit containing components of the formulation. The invention further provides a sustained release formulation for drug substances comprising glutamic acid, or a salt thereof, and an amount of a peptide.

15 Claims, No Drawings
Specification includes a Sequence Listing.

SEQUENCE LISTING

```
<160> NUMBER OF SEQ ID NOS: 20

<210> SEQ ID NO 1
<211> LENGTH: 16
<212> TYPE: PRT
<213> ORGANISM: Artificial Sequence
<220> FEATURE:
<223> OTHER INFORMATION: Synthetic peptide

<400> SEQUENCE: 1

Met Arg Trp Gln Glu Met Gly Tyr Ile Phe Tyr Pro Arg Lys Leu Arg
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Synthetic peptide

<400> SEQUENCE: 2

Met Arg Trp Gln Glu Met Gly Tyr Ile Phe Tyr Phe Arg Lys Leu Arg
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Synthetic peptide

<400> SEQUENCE: 3

Met Gly Trp Gln Glu Met Gly Tyr Ile Phe Tyr Pro Arg Lys Leu Arg
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: Synthetic peptide

<400> SEQUENCE: 4

Met Gly Tyr Ile Phe Tyr Pro Arg Lys Leu Arg
1               5                   10

<210> SEQ ID NO 5
<211> LENGTH: 16
<212> TYPE: PRT
<213> ORGANISM: Artificial Sequence
<220> FEATURE:
<223> OTHER INFORMATION: Synthetic peptide

<400> SEQUENCE: 5

Met Arg Trp Gln Glu Ala Gly Tyr Ile Phe Tyr Pro Arg Lys Leu Arg
1               5                   10                  15

<210> SEQ ID NO 6
<211> LENGTH: 16
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<222> LOCATION: (14)..(14)
<223> OTHER INFORMATION: D-Ala

<400> SEQUENCE: 6

Met Arg Trp Gln Glu Met Gly Tyr Ile Phe Tyr Pro Arg Ala Leu Arg
1               5                   10                  15

<210> SEQ ID NO 7
<211> LENGTH: 13
<212> TYPE: PRT
<213> ORGANISM: Artificial Sequence
<220> FEATURE:
<223> OTHER INFORMATION: Synthetic peptide

<400> SEQUENCE: 7

Met Arg Trp Gln Glu Met Asn Tyr Ile Phe Tyr Pro Arg
1               5                   10

<210> SEQ ID NO 8
<211> LENGTH: 16
<212> TYPE: PRT
<213> ORGANISM: Artificial Sequence
<220> FEATURE:
<223> OTHER INFORMATION: Synthetic peptide

<400> SEQUENCE: 8

Met Arg Trp Gln Glu Met Gly Tyr Ile Phe Tyr Pro Arg Asn Leu Arg
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Synthetic peptide

<400> SEQUENCE: 9

Met Arg Trp Gln Glu Met Gln Tyr Ile Phe Tyr Pro Arg Ala Leu Arg
1               5                   10                  15

<210> SEQ ID NO 10
<211> LENGTH: 12
<212> TYPE: PRT
<213> ORGANISM: Artificial Sequence
<220> FEATURE:
<223> OTHER INFORMATION: Synthetic peptide

<400> SEQUENCE: 10

Arg Trp Gln Glu Met Asn Tyr Ile Phe Tyr Pro Arg
1               5                   10

<210> SEQ ID NO 11
<211> LENGTH: 16
<212> TYPE: PRT
<213> ORGANISM: Artificial Sequence
<220> FEATURE:
<223> OTHER INFORMATION: Synthetic peptide

<400> SEQUENCE: 11

Met Arg Trp Gln Glu Met Gly Tyr Ile Phe Tyr Pro Arg Ala Leu Arg
1               5                   10                  15

<210> SEQ ID NO 12
```

```
<211> LENGTH: 16
<212> TYPE: PRT
<213> ORGANISM: Artificial Sequence
<220> FEATURE:
<223> OTHER INFORMATION: Synthetic peptide

<400> SEQUENCE: 12

Met Arg Trp Gln Glu Met Gly Tyr Ile Phe Tyr Pro Arg Lys Leu Ala
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Synthetic peptide

<400> SEQUENCE: 13

Met Arg Trp Gln Glu Met Gly Tyr Ile Phe Tyr Ala Arg Lys Leu Arg
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic peptide

<400> SEQUENCE: 14

Arg Trp Gln Glu Met Gly Tyr Ile Phe Tyr Pro Arg Gln Leu Arg
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Synthetic peptide

<400> SEQUENCE: 15

Met Arg Trp Gln Glu Glu Gly Tyr Ile Phe Tyr Pro Arg Lys Leu Arg
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic peptide

<400> SEQUENCE: 16

Met Arg Trp Gln Glu Met Gly Tyr Ile Phe Tyr Pro Arg Lys Leu
1               5                   10                  15

<210> SEQ ID NO 17
<211> LENGTH: 13
<212> TYPE: PRT
<213> ORGANISM: Artificial Sequence
<220> FEATURE:
<223> OTHER INFORMATION: Synthetic peptide

<400> SEQUENCE: 17

Glu Arg Trp Gln Glu Ala Gly Tyr Ile Ala Tyr Pro Arg
1               5                   10

<210> SEQ ID NO 18
<211> LENGTH: 12
```

```
<212> TYPE: PRT
<213> ORGANISM: Artificial Sequence
<220> FEATURE:
<223> OTHER INFORMATION: Synthetic peptide

<400> SEQUENCE: 18

Arg Trp Gln Glu Met Gln Tyr Ile Phe Tyr Pro Arg
1               5                   10

<210> SEQ ID NO 19
<211> LENGTH: 16
<212> TYPE: PRT
<213> ORGANISM: Artificial Sequence
<220> FEATURE:
<223> OTHER INFORMATION: Synthetic peptide

<400> SEQUENCE: 19

Met Arg Trp Gln Glu Met Gly Tyr Ile Phe Tyr Pro Ala Lys Leu Arg
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid with a non-polar side
      chain or a polar side chain or is absent
<220> FEATURE:
<221> NAME/KEY: MISC_FEATURE
<222> LOCATION: (2)..(2)
<223> OTHER INFORMATION: Xaa at position 2 is Arg or absent.  Xaa at
      position 2 is Arg if Xaa at position 1 is an amino acid with a
      non-polar side chain or a polar side chain.
<220> FEATURE:
<221> NAME/KEY: MISC_FEATURE
<222> LOCATION: (3)..(3)
<223> OTHER INFORMATION: Xaa at position 3 is Trp if Xaa at position 2
      is Arg. Xaa at position 3 is absent if Xaa at position 2 is
      absent.
<220> FEATURE:
<221> NAME/KEY: MISC_FEATURE
<222> LOCATION: (6)..(6)
<223> OTHER INFORMATION: Xaa is an amino acid with a non-polar side
      chain or a polar side chain
<220> FEATURE:
<221> NAME/KEY: MISC_FEATURE
<222> LOCATION: (7)..(7)
<223> OTHER INFORMATION: Xaa is an amino acid with a non-polar side
      chain or a polar side chain
<220> FEATURE:
<221> NAME/KEY: MISC_FEATURE
<222> LOCATION: (10)..(10)
<223> OTHER INFORMATION: Xaa is an amino acid with a non-polar side
      chain
<220> FEATURE:
<221> NAME/KEY: MISC_FEATURE
<222> LOCATION: (12)..(12)
<223> OTHER INFORMATION: Xaa is an amino acid with a non-polar side
      chain
<220> FEATURE:
<221> NAME/KEY: MISC_FEATURE
<222> LOCATION: (14)..(14)
<223> OTHER INFORMATION: Xaa is Lys or an amino acid with a non-polar
      side chain or is absent
<220> FEATURE:
<221> NAME/KEY: MISC_FEATURE
<222> LOCATION: (15)..(15)
<223> OTHER INFORMATION: Xaa at position 15 is Leu or absent.  Xaa at
      position 15 is absent when Xaa at position 14 is absent.
<220> FEATURE:
<221> NAME/KEY: MISC_FEATURE
```

```
-continued

<222> LOCATION: (16)..(16)
<223> OTHER INFORMATION: Xaa at position 16 is Arg when Xaa 14 is an
      amino acid with a non-polar side chain.  Xaa at position 16 is an
      amino acid with a non-polar side chain or is absent when Xaa 14 is
      Lys.  Xaa at position 16 is absent  when Xaa at position 14 is
      absent

<400> SEQUENCE: 20

Xaa Arg Trp Gln Glu Xaa Xaa Tyr Ile Xaa Tyr Xaa Arg Xaa Leu Xaa
1               5                   10                  15
```

PEPTIDE-CONTAINING FORMULATIONS

CROSS REFERENCES TO RELATED APPLICATIONS

This application is a U.S. National Phase of International Application No. PCT/US2019/024331, filed Mar. 27, 2019, which claims priority benefit of U.S. Provisional Application No. 62/648,746, filed on Mar. 27, 2018, which is hereby incorporated by reference in its entirety and for all purposes as if fully set forth herein.

INCORPORATION BY REFERENCE OF MATERIAL SUBMITTED ELECTRONICALLY

Incorporated by reference in its entirety is a computer-readable nucleotide/amino acid sequence listing identified as follows: name of ASCII text file: 52074A SubSeqlisting.txt, date of creation: Dec. 22, 2020, file size: 6,819 bytes.

BACKGROUND

Among adults aged 20 years or more in the United States, more than one third were obese during 2011-2014 (Ogden et al., Prevalence of Obesity Among Adults and Youth: United States, 2011-2014), NCHS Data Brief, No. 219 (November 2015). The prevalence of obesity among children in the U.S. (aged 2-19 years) was 17% during this timeframe. (Ogden, 2015, supra). Obesity is a risk factor for the development of numerous health problems, including metabolic syndrome, insulin resistance, type 2 diabetes, fatty liver disease, cardiovascular disease, obstructive sleep apnoea, stroke, hypertension, osteoarthritis, reproductive problems, and cancer (National Heart, Lung, and Blood Institute article: http://www.nhlbi.nih.gov/health/health-topics/topics/obe/risks).

Diabetes, an obesity-related condition, was the $7^{th}$ leading cause of death in the U.S. in 2010. In 2012, 9.3% of the American population (or 29.1 million people) had diabetes, and approximately 208,000 children in the U.S. were estimated to have diagnosed diabetes. Every year, 1.4 million people in the U.S. are diagnosed with diabetes. Diabetes is associated with several complications and co-morbid conditions, including hypoglycemia, hypertension, dyslipidemia, cardiovascular disease, stroke, blindness, diabetic retinopathy, kidney disease, and amputations. According to the American Diabetes Association, the estimated total cost of diagnosed diabetes in the U.S. in 2012 was $245 billion (Diabetes Care 36: 1033-1046 (April 2013)). This cost highlights the substantial burden that diabetes imposes on the American society.

Non-alcoholic fatty liver disease (NAFLD) is a condition of excessive fat accumulation in the form of triglycerides (steatosis) in the liver. NAFLD is the most common form of chronic liver disease in the United States, affecting as many as 80 million people, particularly those in their 40s and 50s. In addition to liver-related morbidity and mortality, there is growing evidence that NAFLD is a multisystem disease, with increased risk of type-2 diabetes mellitus, cardiovascular and cardiac diseases, cancer, and chronic kidney disease. While the majority of deaths among NAFLD patients are attributable to cardiovascular disease, as many as 15 million people in the US also have liver cell injury and inflammation, a condition called NASH (Non-Alcoholic SteatoHepatitis). NASH most often occurs in persons who are middle-aged and overweight or obese, ranks as one of the major causes of cirrhosis in America, and is predicted to become the most frequent indication for liver transplantation by 2030. There are currently no approved drugs for the treatment of NASH.

BRIEF SUMMARY OF THE INVENTION

A formulation comprising glutamic acid, or a salt thereof, and an effective amount of a peptide is provided. The invention also provides a method of preparing the formulation, methods of treating a condition using the formulation, and a kit containing components of the formulation. The invention further provides a sustained release formulation for drug substances comprising glutamic acid, or a salt thereof, and an amount of a peptide.

Aspects of the invention that have been described herein as methods also can be described as "uses," and all such uses are contemplated as aspects of the invention. Likewise, compositions described herein as having a "use" can alternatively be described as processes or methods of using, which are contemplated as aspects of the invention.

Likewise, details of the invention that are described herein in relation to a particular method, use, composition, or other product should be understood to be applicable to other aspects or embodiments of the invention, including aspects or embodiments considered to be different classes of invention for examination or other purposes.

The invention includes, as an additional aspect, all embodiments of the invention narrower in scope in any way than the variations defined by specific paragraphs above. For example, where certain aspects of the invention that are described as a genus or set, it should be understood that every member of a genus or set is, individually, an aspect of the invention. Likewise, every individual subset is intended as an aspect of the invention. By way of example, if an aspect of the invention is described as a members selected from the group consisting of 1, 2, 3, and 4, then each individual subgroup (e.g., members selected from {1,2,3} or {1,2,4} or {2,3,4} or {1,2} or {1,3} or {1,4} or {2,3} or {2,4} or {3,4}) and each individual species {1} or {2} or {3} or {4} is contemplated as an aspect or variation of the invention. Likewise, if an aspect of the invention is characterized as a range, such as a temperature range or concentration range, then integer sub-ranges are contemplated as aspects or variations of the invention. For ranges defined as "between" two endpoints, the range is intended to be inclusive of the endpoints.

The headings herein are for the convenience of the reader and not intended to be limiting. Additional aspects, embodiments, and variations of the invention will be apparent from the Detailed Description and/or claims.

Although the Applicant invented the full scope of the invention described herein, the Applicant does not intend to claim subject matter described in the prior art work of others. Therefore, in the event that statutory prior art within the scope of a claim is brought to the attention of the Applicant by a Patent Office or other entity or individual, the Applicant reserves the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

DETAILED DESCRIPTION OF THE INVENTION

The invention relates to the identification of glutamic acid, or a salt thereof, as an agent for preventing gelling of peptide solutions.

A mitochondrial-derived peptide called MOTS-c, derived from an open reading frame of the 12S rRNA-c, and some of its properties are described in Lee et al., Cell Metabolism, 21(3):443-54 (3 Mar. 2015), and U.S. Patent Publication No. 2017/0049853, peptide described as MOTS3, both incorporated herein by reference in their entirety and for their specific teachings of MOTS-c structures and activities. Human MOTS-c has the amino acid sequence MRWQEMGYIFYPRKLR (SEQ ID NO: 1). In some variations, the invention relates to formulations of a MOTS-c peptide, including a human MOTS-c peptide. For example, the invention includes glutamic acid formulations of a peptide that comprises or consists of the amino acid sequence set forth in SEQ ID NO: 1.

In exemplary embodiments, the invention relates to a formulation that contains high concentrations of peptide. The invention also provides a formulation that contains high concentrations of a MOTS-c analog peptide. Exemplary MOTS-c analog peptides suitable for formulation according to the invention include peptides described in International Patent Application No. PCT/US2017/053597, filed 27 Sep. 2017, published as WO 2018/064098 on 5 Apr. 2018, incorporated herein by reference in its entirety and in particular for its teachings of peptides and peptide properties.

In still additional embodiments, the invention includes formulations of peptides conjugated to at least one heterologous moiety, e.g., as described in PCT/US2017/053597, incorporated here by reference. For example, the peptide can be lipidated (e.g., myritoylated, palmitoylated, linked to a C7-C20 lipid moiety), glycosylated, amidated, carboxylated, phosphorylated, esterified, acylated, acetylated, cyclized, pegylated, dimerized, polymerized, attached to a targeting moiety, or otherwise conjugated.

In exemplary embodiments, the invention relates to a peptide formulation that is stable for a minimum of three days at room temperature. In exemplary embodiments, the invention relates to a formulation that is a clear liquid or gel free for a minimum of three days at room temperature.

In exemplary embodiments, the invention relates to a peptide formulation that one can administer to a patient through a standard gauge needle. For example, a standard gauge needle is about 27 gauge.

In exemplary embodiments, the invention relates to a peptide formulation that can be lyophilized to form a solid formulation for reconstitution prior to administration.

Lyophilized forms of formulations described herein are embodiments of the invention. Lyophilized forms are stable at low temperatures, e.g., −70° C. and above, as well as room temperature. Stability of lyophilized formulations has been established at room temperature for longer periods than achievable with the same formulation in solution.

In exemplary embodiments, the invention relates to a formulation that comprises glutamic acid, or a salt thereof, as a solubilizer.

In exemplary embodiments, said glutamic acid is present in an aqueous form of the pharmaceutical formulation in a concentration of between about 15 and about 100 mM, preferably between about 25 mM and about 50 mM, and even more preferably about 50 mM.

In exemplary embodiments, the invention relates to a formulation selected from a formulation comprising a peptide concentration of about 25 mg/mL and an L-glutamic acid concentration of about 25 mM; a peptide concentration of about 50 mg/mL and an L-glutamic acid concentration of about 50 mM; or a peptide concentration of about 75 mg/mL and an L-glutamic acid concentration of about 75 mM.

In exemplary embodiments, the glutamic acid employed may be in the L-form. Glutamic acid in the invention also includes its various glutamate salt forms. Glutamate salts include, for example, sodium glutamate. Other salts can be used, for example, potassium, ammonium, calcium or magnesium salts of glutamate, as well as others known in the art. A highly purified form of a formulation component, for example glutamic acid, refers to pharmaceutical grade purity level, which is sufficiently pure to administer to a human such that it is devoid of contaminants so as to be safe and non-toxic. L-glutamic acid is commercially available in purified form and can be obtained from Ajinomoto AminoScience LLC, NC, USA or from J.T. Baker.

In exemplary embodiments, said aqueous form of the pharmaceutical formulation has a pH of between 3 and 7, preferably between 4 and 7, more preferably about 4.

In exemplary embodiments, the peptide of the present disclosure comprises an amino acid sequence of Formula I:

$$X^1\text{-Q-E-}X^2\text{-}X^3\text{-Y-I-}X^4\text{-Y-}X^5\text{-R-}X^6 \quad \text{(I) (SEQ ID NO: 20)}$$

or a pharmaceutically acceptable salt thereof; wherein $X^1$ is absent or if present is $X^7$—RW—, wherein $X^7$ is absent or if present is an amino acid with a non-polar side chain or a polar side chain; $X^2$ and $X^3$ are each independently an amino acid with a non-polar side chain or a polar side chain; $X^4$ and $X^5$ are each independently an amino acid with a non-polar side chain; $X^6$ is absent or if present is -KL-$X^8$ or -$X^9$-LR, wherein $X^8$ is absent or if present is an amino acid with a non-polar side chain and $X^9$ is an amino acid with a non-polar side chain; provided that the peptide is none of: MRWQEMGYIFYPRKLR (SEQ ID NO: 1); MRWQEMGYIFYFRKLR (SEQ ID NO: 2); MGWQEMGYIFYPRKLR (SEQ ID NO: 3); and/or MGYIFYPRKLR (SEQ ID NO: 4).

In exemplary embodiments, the peptide comprises an amino acid sequence of Formula I, wherein $X^1$ is absent or if present is $X^7$—RW—, wherein $X^7$ is absent or if present is selected from D, (dD), E, (dE), K, (dK), R, (dR), H, (dH), N, (dN), Q, (dQ), S, (dS), T, (dT), Y, (dY), C, (dC), G, A, (dA), V, (dV), L, (dL), I, (dl), F, (dF), W, (dW), P (dP), M and (dM); $X^2$ and $X^3$ are each independently selected from D, (dD), E, (dE), K, (dK), R, (dR), H, (dH), N, (dN), Q, (dQ), S, (dS), T, (dT), Y, (dY), C, (dC), G, A, (dA), V, (dV), L, (dL), I, (dl), F, (dF), W, (dW), P (dP), M and (dM); $X^4$ and $X^5$ are each independently selected from G, A, (dA), V, (dV), L, (dL), I, (dl), F, (dF), W, (dW), P (dP), M and (dM); $X^6$ is absent or if present is -KL-$X^8$ or -$X^9$-LR, wherein $X^8$ is absent or if present is selected from G, A, (dA), V, (dV), L, (dL), I, (dl), F, (dF), W, (dW), P (dP), M and (dM) and $X^9$ is selected from G, A, (dA), V, (dV), L, (dL), I, (dl), F, (dF), W, (dW), P (dP), M and (dM); or a pharmaceutically acceptable salt thereof.

In exemplary embodiments, the peptide comprises an amino acid sequence of Formula I wherein $X^1$ is absent or if present is $X^7$—RW—, wherein $X^7$ is absent or if present is M or E; $X^2$ is M, A or E; $X^3$ is G, N or Q; $X^4$ is F or A; $X^5$ is P or A; $X^6$ is absent or if present is -KL-$X^8$ or -$X^9$-LR, wherein $X^8$ is absent or if present is R or A and $X^9$ is selected from K, A, (dA), N and Q; or a pharmaceutically acceptable salt thereof.

In exemplary embodiments, the peptide comprises an amino acid sequence selected from the group consisting of: MRWQEAGYIFYPRKLR (SEQ ID NO: 5); MRWQEMGYIFYPR(dA)LR (SEQ ID NO: 6); MRWQEMNYIFYPR (SEQ ID NO: 7); MRWQEMGYIFYPRNLR (SEQ ID NO: 8); MRWQEMQYIFYPRALR (SEQ ID NO: 9); RWQEMNYIFYPR (SEQ ID NO: 10);

MRWQEMGYIFYPRALR (SEQ ID NO: 11); MRWQEMGYIFYPRKLA (SEQ ID NO: 12); MRWQEMGYIFYARKLR (SEQ ID NO: 13); RWQEMGYIFYPRQLR (SEQ ID NO: 14); MRWQEEGYIFYPRKLR (SEQ ID NO: 15); MRWQEMGYIFYPRKL (SEQ ID NO: 16); ERWQEAGYIAYPR (SEQ ID NO: 17); RWQEMQYIFYPR (SEQ ID NO: 18); and MRWQEMGYIFYPAKLR (SEQ ID NO: 19); and a pharmaceutically acceptable salt thereof.

In exemplary embodiments, the peptide comprises the amino acid sequence RWQEMNYIFYPR (SEQ ID NO: 10); and a pharmaceutically acceptable salt thereof.

As used herein, the term "high temperature" shall refer to a storage temperature which is higher than 0° C. Preferably, said high temperature is higher than a temperature selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40° C.

As used herein, the term "long term storage" shall refer to storage of a composition comprising the pharmaceutical formulation for 1 day or more, preferably for 2, 3, 4, 5, 6, 7, 8, 9, 10, 11, 12, 13, 14, 15, 16, 17, 18, 19, 20, 21, 22, 23 days or more, or even 1 month or more.

For lyophilized formulations, initial experiments have shown stability for at least 12 weeks at temperatures of −70° C., 5° C., and 25° C. Lyophilized formulations are contemplated that are stable for at least 4, 8, 12, 16, 20, 24, 28, 32, 36, 40, 44, 48, 52 weeks, 104 weeks, or more. Lyophilized formulations stable for 1-104 weeks, or integer sub-ranges thereof, are specifically contemplated.

In exemplary embodiments, said aqueous form of the pharmaceutical formulation is a solution stable at conditions designed for practical use (i.e., at a temperature suitable for administration) for more than 1 day.

As used herein, the term "formulation(s)" means a composition of matter that comprises a combination of at least one active ingredient with one or more other ingredients for one or more particular uses, such as storage, further processing, sale, and/or administration to a subject, such as, for example, administration to a subject of a specific agent in a specific amount, by a specific route, to treat a specific disease. In some embodiments, "formulation" refers to a composition or admixture of a biopharmaceutical and a pharmaceutically acceptable medium that is compatible with the biopharmaceutical that can be administered to humans or animals.

As used herein, the term "effective amount" when used in reference to a therapeutic peptide is intended to mean an amount of the therapeutic molecule sufficient to ameliorate or mitigate at least one symptom associated with a targeted disease or physiological condition.

Peptide gelling is induced by long term storage and/or storage at high temperatures. Formulation materials and methods described herein reduce, slow, delay the onset of, and/or eliminate the gelling.

In exemplary embodiments, the peptide is formulated with an excipient to provide a pharmaceutical composition which composition can be used to treat a disease in a patient or another medical condition.

As used herein, the term "excipient" is intended to mean a therapeutically inactive substance. Excipients can be included in a formulation for a wide variety of purposes including, for example, as a diluent, vehicle, buffer, stabilizer, tonicity agent, bulking agent, surfactant, cryoprotectant, lyoprotectant, anti-oxidant, metal ion source, chelating agent and/or preservative. Excipients include, for example, polyols such as sorbitol or mannitol; sugars such as sucrose, lactose or dextrose; polymers such as polyethylene glycol; salts such as NaCl, KCl or calcium phosphate, amino acids, for example, proline, glycine or methionine, surfactants, metal ions, buffer salts such as glutamate, acetate or aspartate, preservatives and polypeptides such as human serum albumin, as well as saline and water. Excipients can comprise sugars, for example sugar alcohols, reducing sugars, non-reducing sugars and sugar acids. Excipients are well known in the art and can be found described in, for example, Wang W., Int. J. Pharm. 185:129-88 (1999) and Wang W., Int. J. Pharm. 203:1-60 (2000).

In various embodiments, the formulation can include one or more excipients. One potential role of an included excipient is to provide stabilization of the biopharmaceutical against stresses that can occur during manufacturing, shipping and storage. To accomplish this, at least one excipient can function as a buffer, stabilizer, tonicity agent, bulking agent, surfactant, cryoprotectant, lyoprotectant, anti-oxidant, metal ion source, chelating agent and/or preservative. In addition, at least one excipient can function as a diluent and/or vehicle or be employed to reduce viscosity in high concentration formulations in order to enable their delivery and/or enhance patient convenience.

Various excipients that can be useful in either a liquid or lyophilized formulation comprise, fucose, cellobiose, maltotriose, melibiose, octulose, ribose, xylitol, arginine, histidine, glycine, alanine, methionine, glutamic acid, lysine, imidazole, glycylglycine, mannosylglycerate, Triton X-100, Pluoronic F-127, cellulose, cyclodextrin, dextran (10, 40 and/or 70 kD), polydextrose, maltodextrin, ficoll, gelatin, hydroxypropylmeth, sodium phosphate, potassium phosphate, $ZnCl_2$, zinc, zinc oxide, sodium citrate, trisodium citrate, tromethamine, copper, fibronectin, heparin, human serum albumin, protamine, glycerin, glycerol, EDTA, meta-cresol, benzyl alcohol and phenol. Various excipients known in the art are described in, for example, Wang W., Int. J. Pharm. 185:129-88 (1999) and Wang W., Int. J. Pharm. 203:1-60 (2000).

As used herein, "preservative" refers to a compound that can be added to a formulation to help maintain stability of the peptide over time by, for example, reducing the impact of bacterial, fungal or other unwanted organic growth. The addition of a preservative may also facilitate the production of a multi-use (multiple-dose) formulation. Examples of potential preservatives include, but are not limited to, octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as, for example, phenol, butyl and benzyl alcohol, alkyl parabens such as methyl or propyl paraben, catechol, resorcinol, cyclohexanol, 3-pentanol, and m-cresol.

High concentration formulations are required for effective use of therapeutic peptides via any parenteral route, for example via subcutaneous injection or intravenous injection for treatment of various disorders. The disclosed formulations are also intended for treatment of systemic disorders, the treatment of which may require repeated administrations via subcutaneous injection or intravenous injection. Without the availability of a high concentration formulation, systemic administration via subcutaneous injection might not be possible or practical.

Stable solutions with low viscosity, which are free of small particles, are less likely to form aggregates. Such solutions are generally considered to be the result of good formulations. Such solution properties are crucial for peptide formulation at higher concentrations (and especially concentrations above 25 mg/mL).

As used herein, "viscosity" refers to "kinematic viscosity" or "absolute viscosity." "Kinematic viscosity" is a measure of the resistive flow of a fluid under the influence of gravity. Absolute Viscosity=Kinematic Viscosity×Density. Viscosity is concentration dependent. Several previously described formulations consider the highest attainable concentration of peptide to be the concentration at which the viscosity of the solution reaches 20 cP. Using the materials and methods described herein, the viscosity of the formulations described herein reaches 20 cP at a peptide concentration of 10-100 mg/mL. Formulations of therapeutic peptides typically reach a viscosity of 20 cP at concentrations usually less than 100 mg/mL, for example in the range of about 25 to about 75 mg/mL.

Briefly, sugar alcohols, also known as polyols, polyhydric alcohols, or polyalcohols, are hydrogenated forms of carbohydrate having a carbonyl group reduced to a primary or secondary hydroxyl group. Polyols can be used as stabilizing excipients and/or isotonicity agents in both liquid and lyophilized formulations. Polyols can protect biopharmaceuticals from both physical and chemical degradation pathways. Examples of sugar alcohols can include sorbitol, glycerol, mannitol, xylitol, maltitol, lactitol, erythritol and threitol.

Reducing sugars can comprise, for example, sugars with a ketone or aldehyde group and contain a reactive hemiacetal group, which allows the sugar to act as a reducing agent. Specific examples of reducing sugars include fructose, glucose, glyceraldehyde, lactose, arabinose, mannose, xylose, ribose, rhamnose, galactose and maltose. Non-reducing sugars can comprise an anomeric carbon that is an acetal and is not substantially reactive with amino acids or polypeptides to initiate a Maillard reaction. Specific examples of non-reducing sugars include sucrose, trehalose, sorbose, sucralose, melezitose and raffinose. Sugar acids include, for example, saccharic acids, gluconate and other polyhydroxy sugars and salts thereof.

Buffers or buffers in combination with excipients can maintain the pH of liquid formulations throughout product shelf-life and maintain the pH of lyophilized formulations during the lyophilization process and upon reconstitution, for example.

Tonicity agents and/or stabilizers included in liquid formulations can be used, for example, to provide isotonicity, hypotonicity or hypertonicity to a formulation such that it is suitable for administration. Such excipients also can be used to facilitate maintenance of a peptide's structure and/or to minimize electrostatic, solution protein-protein interactions. Examples of tonicity agents and/or stabilizers can include polyols, salts and/or amino acids.

Anti-oxidants are useful in liquid formulations to control protein oxidation and also can be used in lyophilized formulations to retard oxidation reactions.

Metal ions can be included in a liquid formulation, for example, as a co-factor and divalent cations such as zinc and magnesium can be utilized in suspension formulations. Chelating agents included in liquid formulations can be used, for example, to inhibit metal ion catalyzed reactions. With respect to lyophilized formulations, metal ions also can be included, for example, as a co-factor. Although chelating agents are generally omitted from lyophilized formulations, they also can be included as desired to reduce catalytic reactions during the lyophilization process and upon reconstitution.

Stability of a formulation refers to the retention of structure and/or function and/or biological activity of a biopharmaceutical within the formulation. The retention of structure and/or function and/or biological activity does not need to be 100%. Measurement of the stability of a formulation can be a comparative measure. Therefore, if one formulation is said to be more stable or have greater stability than another, the formulation with greater stability has retained a greater percentage of a desired characteristic being investigated than the other formulation, unless the characteristic being considered is a negative characteristic. If the characteristic is a negative characteristic, then the formulation with greater stability will have less of that characteristic. For example, formulation A is more stable than formulation B if it has a lower propensity to form a gel than formulation B during storage.

In various embodiments, the stability of a peptide within a formulation can comprise the retention of physical and/or chemical stability. Biopharmaceutical stability can be assessed by, for example, determining whether the biopharmaceutical has been subjected to a physical degradation and/or chemical degradation pathway, including chemical modification of its structure. Retention of stability can also be measured, for example, in terms of the extent of gelling, after storage at different temperatures or after multiple freeze-thaw cycles. These measurements can reflect the amount of peptide aggregation.

Stability of a peptide formulation can be evaluated by multiple criteria as described herein. In some variations, stability is evinced by purity. One indicia of purity is quantification of major and minor forms, e.g., with chromatographic analysis (such as RP-HPLC or ion exchange HPLC). In some variations, purity is at least 90%, 91%, 92%, 93%, 94%, 95%, 96%, 97% 98%, or 99% as evaluated by the areas of major versus minor chromatographic peaks. Purities in the range of 90-99.5%, including integer and half-integer subranges thereof, are specifically contemplated. In some variations, stability is evinced by properties of the peptide in solution, including stable pH, minimal or absence of turbidity (e.g., when evaluated at 400-700 nm), minimal or absence of particles, and/or minimal or absence of discoloration. In some variations, stability is evinced by retention of biological activity, e.g., in cell based assays or animal models. In some variations, purity is evinced by a plurality of these criteria.

Preservatives in liquid formulations can be used, for example, to protect against microbial growth and are particularly beneficial in multi-dose formulations. In lyophilized formulations, preservatives are generally included in the reconstitution diluent. Benzyl alcohol is a specific example of a preservative useful in a formulation of the invention.

As used herein, the term "surfactant" is intended to mean a substance that functions to reduce the surface tension of a liquid in which it is dissolved. Surfactants can be included in a formulation for a variety of purposes including, for example, to prevent or control aggregation, particle formation and/or surface adsorption in liquid formulations or to prevent or control these phenomena during the lyophilization and/or reconstitution process in lyophilized formulations. Surfactants include, for example, amphipathic organic compounds that exhibit partial solubility in both organic solvents and aqueous solutions. General characteristics of surfactants include their ability to reduce the surface tension of water, reduce the interfacial tension between oil and water and also form micelles. Surfactants of can include non-ionic and ionic surfactants. Surfactants are known in the art and can be found described in, for example, Randolph T. W. and Jones L. S., Surfactant-protein interactions. Pharm Biotechnol. 13:159-75 (2002).

Non-ionic surfactants can include, for example, alkyl poly (ethylene oxide), alkyl polyglucosides such as octyl glucoside and decyl maltoside, fatty alcohols such as cetyl alcohol and oleyl alcohol, cocamide MEA, cocamide DEA, and cocamide TEA. Specific examples of non-ionic surfactants include the polysorbates including, for example, polysorbate 20, polysorbate 28, polysorbate 40, polysorbate 60, polysorbate 65, polysorbate 80, polysorbate 81, polysorbate 85 and the like; the poloxamers including, for example, poloxamer 188, also known as poloxalkol or poly(ethylene oxide)-poly(propylene oxide), poloxamer 407 or polyethylene-polypropylene glycol and the like, and polyethylene glycol (PEG). Polysorbate 20 is synonymous with TWEEN 20, sorbitan monolaurate and polyoxyethylenesorbitan monolaurate.

Ionic surfactants can include, for example, anionic, cationic and zwitterionic surfactants. Anionic surfactants include, for example, sulfonate-based or carboxylate-based surfactants such as soaps, fatty acid salts, sodium dodecyl sulfate (SDS), ammonium lauryl sulfate and other alkyl sulfate salts. Cationic surfactants include, for example, quaternary ammonium-based surfactants such as cetyl trimethylammonium bromide (CTAB), other alkyltrimethylammonium salts, cetyl pyridinium chloride, polyethoxylated tallow amine (POEA) and benzalkonium chloride. Zwitterionic or amphoteric surfactants include, for example, dodecyl betaine, dodecyl dimethylamine oxide, cocamidopropyl betaine and coco ampho carboxy glycinate.

In various embodiments, the formulation also includes a drug substance.

In various embodiments, the formulation forms a sustained release matrix in vivo.

In various embodiments, the formulation forms a sustained-release matrix upon subcutaneous injection or intramuscular injection.

In various embodiments, the release of said drug substance is over a period of greater than about four hours. In various embodiments, the release of said drug substance is over a period of greater than about eight hours. In various embodiments, the release of said drug substance is over a period of greater than about twelve hours. In various embodiments, the release of said drug substance is over a period of greater than about twenty-four hours. In various embodiments the release of said drug substance is longer than a period of seven 7 days. In various embodiments, the pharmacological effect from at least one of said drug substance lasts at least about four hours. In various embodiments, the pharmacological effect from at least one of said drug substance lasts at least about eight hours. In various embodiments, the pharmacological effect from at least one of said drug substance lasts at least about twelve hours. In various embodiments, the pharmacological effect from at least one of said drug substance lasts at least about twenty-four hours.

"Sustained release dosage forms" or "sustained release matrix" mean forms designed to release a drug at a predetermined rate by maintaining a constant drug level for a specific period of time with minimum side effects. The basic rationale of sustained release drug delivery system optimizes the biopharmaceutical, pharmacokinetic and pharmacodynamics properties of a drug in such a way that its utility is maximized, side-effects are reduced and cure and/or treatment of the disease is better achieved.

The terms "drug substance", "active pharmaceutical ingredient ("API"). "pharmacologically active agent" "drug" and "agent" are used interchangeably herein to refer to any chemical compound, complex or composition that has a beneficial biological effect, generally a therapeutic effect in the treatment of a disease or abnormal physiological condition. These terms also encompass pharmaceutically acceptable, pharmacologically active derivatives of those drug substances specifically mentioned herein, including, but not limited to, salts, esters, amides, pro-drugs, active metabolites, isomers, fragments, analogs, coordination compounds and complexes, and the like. When the terms "drug substance", active pharmaceutical ingredient ("API"), "pharmacologically active agent" "drug" and "agent" are used, then, or when a particular active agent is specifically identified, it is to be understood that applicants intend to include the active agent per se as well as pharmaceutically acceptable, pharmacologically active salts, esters, amides, pro-drugs, active metabolites, isomers, fragments, analogs, coordination compounds and complexes, and the like.

The drug substances that may be administered using the pharmaceutical formulations of the present invention are not limited, as the invention enables the effective delivery of a wide variety of drug substances. Therefore, the drug substance(s) administered may be selected from any of the various classes of such drug substances including, but not limited to, analgesic agents, anesthetic agents, anti-anginal agents, antiarthritic agents, antiarrhythmic agents, anti-asthmatic agents, antibacterial agents, anti-BPH agents, anticancer agents, anticholinergic agents, anticoagulants, anticonvulsants, antidepressants, antidiabetic agents, antidiarrheals, anti-epileptic agents, antifungal agents, anti-gout agents, anti-helminthic agents, antihistamines, antihypertensive agents, anti-inflammatory agents, antimalarial agents, antimigraine agents, anti-muscarinic agents, anti-nauseants, antineoplastic agents, anti-obesity agents, anti-osteoporosis agents, anti-parkinsonism agents, antiprotozoal agents, antipruritics, antipsychotic agents, antipyretics, antispasmodics, antithyroid agents, antitubercular agents, antiulcer agents, anti-urinary incontinence agents, antiviral agents, anxiolytics, appetite suppressants, attention deficit disorder (ADD) and attention deficit hyperactivity disorder (ADHD) drugs, calcium channel blockers, cardiac inotropic agents, beta-blockers, central nervous system stimulants, cognition enhancers, corticosteroids, COX-2 inhibitors, decongestants, diuretics, gastrointestinal agents, genetic materials, histamine receptor antagonists, hormonolytics, hypnotics, hypoglycemic agents, immunosuppressants, keratolytics, leukotriene inhibitors, lipid-regulating agents, macrolides, mitotic inhibitors, muscle relaxants, narcotic antagonists, nutraceuticals, neuroleptic agents, nicotine, nutritional oils, parasympatholytic agents, sedatives, sex hormones, sympathomimetic agents, tranquilizers, vasodilators, vitamins, and combinations thereof. Some agents, as will be appreciated by those of ordinary skill in the art, and as may be deduced from the discussion below, are encompassed by two or more of the aforementioned groups.

The drug substance can be hydrophobic, amphiphilic, or hydrophilic. The intrinsic water solubility of those drug substances referred to as "hydrophobic" herein, i.e., the aqueous solubility of the drug substances in electronically neutral, non-ionized form, is generally less than 1% by weight, and typically less than 0.1% or 0.01% by weight. Hydrophilic and amphiphilic drug substances herein (which, unless otherwise indicated, are collectively referred to herein as "hydrophilic" drug substances) have apparent water solubilities of at least 0.1% by weight, and typically at least 1% by weight. Both hydrophobic drug substances and hydrophilic drug substances may be selected from any of the drug substance classes, without limitation, enumerated herein. In another method of classifying the solubility of such agents, the agent(s) selected for formulating into a formulation of the present invention may have high solubility; moderate solubility; low solubility; low to moderate solubility; or moderate to high solubility. Likewise, drug substances within these solubility classes may be selected from any of the drug substance classes, without limitation, enumerated herein. When two or more drug substances, for example, are selected for use in the present formulations, each such drug substance may be from different solubility classes.

Among the various drug substance prescription and/or over-the-counter categories referenced hereinabove, the following non-limiting examples are provided: anti-inflammatory drug substances and non-opioid analgesics including, for example and without limitation, aloxiprin, auranofin, azapropazone, azathioprine, benorylate, butorphenol, capsaicin, celecoxib, diclofenac, diflunisal, esonarimod, etodolac, fenbufen, fenoprofen calcium, flurbiprofen, ibuprofen, indomethacin, ketoprofen, ketorolac, leflunomide, meclofenamic acid, mefenamic acid, nabumetone, naproxen, novantrone, oxaprozin, oxyphenbutazone, parecoxib, phenylbutazone, piclamilast, piroxicam, rofecoxib, ropivacaine, sulindac, tetrahydrocannabinol, tramadol, tromethamine, valdecoxib, and ziconotide, as well as the urinary analgesics phenazopyridine and tolterodine; anti-angina drug substances including, for example and without limitation, mibefradil, refludan, nahnefene, carvedilol, cromafiban, lamifiban, fasudil, ranolazine, tedisamil, nisoldipine, and tizanidine; antihelminthics including, for example and without limitation, albendazole, bephenium hydroxynaphthoate, cambendazole, dichlorophen, ivermectin, mebendazole, oxamniquine, oxfendazole, oxantel embonate, praziquantel, pyrantel embonate and thiabendazole; anti-arrhythmic agents, such as amiodarone, disopyramide, flecainide acetate and quinidine sulfate; anti-asthma drug substances including, for example and without limitation, zileuton, zafirlukast, terbutaline sulfate, montelukast, and albuterol; anti-bacterial drug substances including, for example and without limitation, alatrofloxacin, azithromycin, baclofen, benethamine penicillin, cinoxacin, ciprofloxacin, clarithromycin, clofazimine, cloxacillin, demeclocycline, dirithromycin, doxycycline, erythromycin, ethionamide, furazolidone, grepafloxacin, imipenem, levofloxacin, lorefloxacin, moxifloxacin, nalidixic acid, nitrofurantoin, norfloxacin, ofloxacin, rifampicin, rifabutine, rifapentine, sparfloxacin, spiramycin, sulphabenzamide, sulphadoxine, sulphamerazine, sulphacetamide, sulphadiazine, sulphafurazole, sulphamethoxazole, sulphapyridine, tetracycline, trimethoprim, trovafloxacin, and vancomycin; anti-cancer drug substances and immunosuppressants including, for example and without limitation, alitretinoin, aminoglutethimide, amsacrine, anastrozole, azathioprine, bexarotene, bicalutamide, biricodar, bisantrene, busulfan, camptothecin, candoxatril, capecitabine, cytarabine, chlorambucil, cyclosporin, dacarbazine, decitabine, ellipticine, estramustine, etoposide, gemcitabine, irinotecan, lasofoxifene, letrozole, lomustine, melphalan, mercaptopurine, methotrexate, mitomycin, mitotane, mitoxantrone, mofetil, mycophenolate, nebivolol, nilutamide, paclitaxel, palonosetron, procarbazine, ramipril, rubitecan, sirolimus, tacrolimus, tamoxifen, teniposide, testolactone, thalidomide, tirapazamine, topotecan, toremifene citrate, vitamin A, vitamin A derivatives, and zacopride; anti-coagulants and other drug substancess for preventing and treating stroke including, for example and without limitation, cilostazol, citicoline, clopidogrel, cromafiban, dexanabinol, dicumarol, dipyridamole, nicoumalone, oprelvekin, perindopril erbumine, phenindione, ramipril, repinotan, ticlopidine, tirofiban, and heparin, including heparin salts formed with organic or inorganic bases, and low molecular weight heparin, i.e., heparin fragments generally having a weight average molecular weight in the range of about 1000 to about 10,000 D and exemplified by enoxaparin, dalteparin, danaproid, gammaparin, nadroparin, ardeparin, tinzaparin, certoparin, and reviparin; anti-diabetic drug substances include, for example and without limitation, acetohexamide, chlorpropamide, ciglitazone, farglitazar, glibenclamide, gliclazide, glipizide, glucagon, glyburide, glymepiride, miglitol, nateglinide, pimagedine, pioglitazone, repaglinide, rosiglitazone, tolazamide, tolbutamide, triampterine, troglitazone and voglibose; anti-epileptics including, for example and without limitation, beclamide, carbamazepine, clonazepam, ethotoin, felbamate, fosphenytoin, lamotrigine, methoin, methsuximide, methylphenobarbitone, oxcarbazepine, paramethadione, phenacemide, phenobarbitone, phenytoin, phensuximide, primidone, sulthiame, tiagabine, topiramate, valproic acid, and vigabatrin; anti-fungal drug substances including, for example and without limitation, amphotericin, butenafine, butoconazole nitrate, clotrimazole, econazole nitrate, fluconazole, flucytosine, griseofulvin, itraconazole, ketoconazole, miconazole, natamycin, nystatin, sulconazole nitrate, oxiconazole, terbinafine, terconazole, tioconazole and undecenoic acid; anti-gout drug substances including, for example and without limitation, allopurinol, probenecid and sulphin-pyrazone; antihistamines and allergy medications including, for example and without limitation, acrivastine, astemizole, chlorpheniramine, cinnarizine, cetirizine, clemastine, cyclizine, cyproheptadine, desloratadine, dexchlorpheniramine, dimenhydrinate, diphenhydramine, epinastine, fexofenadine, flunarizine, loratadine, meclizine, mizolastine, oxatomide, and terfenadine; antihypertensive drug substances include, for example and without limitation, amlodipine, benazepril, benidipine, candesartan, captopril, carvedilol, darodipine, dilitazem, diazoxide, doxazosin, enalapril, epleronone, eposartan, felodipine, fenoldopam, fosinopril, guanabenz, iloprost, irbesartan, isradipine, lercardinipine, lisinopril, losartan, minoxidil, nebivolol, nicardipine, nifedipine, nimodipine, nisoldipine, omapatrilat, phenoxybenzamine, prazosin, quinapril, reserpine, semotiadil, sitaxsentan, terazosin, telmisartan, and valsartan; antimalarials including, for example and without limitation, amodiaquine, chloroquine, chlorproguanil, halofantrine, mefloquine, proguanil, pyrimethamine and quinine sulfate; drug substances for treating headaches, including anti-migraine agents including, for example and without limitation, almotriptan, butorphanol, dihydroergotamine, dihydroergotamine mesylate, eletriptan, ergotamine, frovatriptan, methysergide, naratriptan, pizotyline, rizatriptan, sumatriptan, tonaberstat, and zolmitriptan; anti-muscarinic drug substances including, for example and without limitation, atropine, benzhexol, biperiden, ethopropazine, hyoscyamine, mepenzolate bromide, oxyphencyclimine, scopolamine, and tropicamide; anti-protozoal drug substances including, for example and without limitation, atovaquone, benznidazole, clioquinol, decoquinate, diiodohydroxyquinoline, diloxanide furoate, dinitolmide, furazolidone, metronidazole, nimorazole, nitrofirazone, ornidazole and tinidazole; antithyroid drug substances including, for example and without limitation, carbimazole, paricalcitol, and propylthiouracil; anti-tussives including, for example and without limitation, benzonatate; antiviral drug substances include, for example and without limitation, antiherpes agents acyclovir, famciclovir, foscarnet, ganciclovir, idoxuridine, sorivudine, trifluridine, valacyclovir, and vidarabine, and otherantiviral agents such as abacavir, amantadine, amprenavir, delviridine, didanosine, efavirenz, indinavir, interferon alpha, lamivudine, nelfinavir, nevirapine, ribavirin, rimantadine, ritonavir, saquinavir, stavudine, tipranavir, valganciclovir, zalcitabine, and zidovudine; and other antiviral agents such as abacavir, indinavir, interferon alpha, nelfinavir, ribavirin, rimantadine, tipranavir, ursodeoxycholic acid, and valganciclovir; anxiolytics, sedatives, and hypnotics including, for example and without limitation, alprazolam, amylobarbitone, barbitone, bentazepam, bromazepam, bromperidol, brotizolam, butobarbitone, carbromal, chlordiazepoxide, chlormethiazole, chlorpromazine, chlorprothixene, clonazepam, clobazam, clotiazepam, clozapine, dexmethylphenidate (d-threo-methylphenidate) diazepam, droperidol, ethinamate, flunanisone, flunitrazepam, triflupromazine, flupenthixol decanoate, fluphenazine, flurazepam, gabapentin, gaboxadol, .gamma.-hydroxybutyrate, haloperidol, lamotrigine, lorazepam, lormetazepam, medazepam, meprobamate, mesoridazine, methaqualone, methylphenidate, midazolam, modafinil, molindone, nitrazepam, olanzapine, oxazepam, pentobarbitone, perphenazine pimozide, pregabalin, prochlorperazine, pseudoephedrine, quetiapine, rispiridone, sertindole, siramesine, sulpiride, sunepitron, temazepam, thioridazine, triazolam, zaleplon, Zolpidem, and zopiclone; appetite suppressants, anti-obesity drug substances and drug substances for treatment of eating disorders including, for example and without limitation, amphetamine, bromocriptine, dextroamphetamine, diethylpropion, lintitript, mazindol, methamphetamine, orlistat, phentermine, and topiramate; cardiovascular drug substances including, for example and without limitation, angiotensin converting enzyme (ACE) inhibitors such as enalapril, ramipril, perindopril erbumine, 1-carboxymethyl-3-1-carboxy-3-phenyl-(1S)-propylamino-2,3,4,5-tetra hydro-1H-(3S)-1-benzazepine-2-one, 3-(5-amino-1-carboxy-1S-pentyl)amino-2,3,4,5-tetrahydro-2-oxo-3S-1H-1-ben-zazepine-lacetic acid or 3-(1-ethoxycarbonyl-3-phenyl-(1S)-propylamino)-2,3,4,5-tetrahydro-2-oxo-(-3S)-benzazepi acid monohydrochloride; cardiac glycosides and cardiac inotropes such as amrinone, digoxin, digitoxin, enoximone, lanatoside C, medigoxin, and milrinone; calcium channel blockers such as verapamil, nifedipine, nicardipene, felodipine, isradipine, nimodipine, amlodipine and diltiazem; beta-blockers such as acebutolol, alprenolol, atenolol, labetalol, metoprolol, nadolol, oxyprenolol, pindolol, propafenone, propranolol, esmolol, sotalol, timolol, and acebutolol; antiarrhythmics such as moricizine, dofetilide, ibutilide, nesiritide, procainamide, quinidine, disopyramide, lidocaine, phenytoin, tocainide, mexiletine, flecainide, encainide, bretylium and amiodarone; cardioprotective agents such as dexrazoxane and leucovorin; vasodilators such as nitroglycerin; diuretic agents such as azetazolamide, amiloride, bendroflumethiazide, bumetanide, chlorothiazide, chlorthalidone, ethacrynic acid, furosemide, hydrochlorothiazide, metolazone, nesiritide, spironolactone, and triamterine; and miscellaneous cardiovascular drugs such as monteplase and corlopam; corticosteroids including, for example and without limitation, beclomethasone, betamethasone, budesonide, cortisone, desoxymethasone, dexamethasone, fludrocortisone, flunisolide, fluocortolone, fluticasone propionate, hydrocortisone, methylprednisolone, prednisolone, prednisone and triamcinolone; erectile dysfunction drug substances including, for example and without limitation, pomorphine, phentolamine, and vardenafil; gastrointestinal drug substances including, for example and without limitation, alosetron, bisacodyl, cilansetron, cimetidine, cisapride, diphenoxylate, domperidone, esomeprazole, famotidine, granisetron, lansoprazole, loperamide, mesalazine, nizatidine, omeprazole, ondansetron, prantoprazole, rabeprazole sodium, ranitidine, risperidone, sulphasalazine, and tegaserod; genetic material including, for example and without limitation, nucleic acids, RNA, DNA, recombinant RNA, recombinant DNA, antisense RNA, antisense DNA, ribozymes, ribooligonucleotides, deoxyribonucleotides, antisense ribooligonucleotides, and antisense deoxyribooligonucleotides. Representative genes include those encoding for vascular endothelial growth factor, fibroblast growth factor, Bcl-2, cystic fibrosis transmembrane regulator, nerve growth factor, human growth factor, erythropoietin, tumor necrosis factor, and interleukin-2, as well as histocompatibility genes such as HLA-B7; keratolytics including, for example and without limitation, acetretin, calcipotriene, calcifediol, calcitriol, cholecalciferol, ergocalciferol, etretinate, retinoids, targretin, and tazarotene; Lipid-regulating drug substances that are generally classified as hydrophobic include HMG CoA reductase inhibitors including, for example and without limitation, atorvastatin, simvastatin, fluvastatin, pravastatin, lovastatin, cerivastatin, rosuvastatin, and pitavastatin, as well as other lipid-lowering ("antihyperlipidemic") drug substances such as 1-methylnicotinamide chloride (1-MNA) HCl, bezafibrate, beclobrate, binifibrate, ciprofibrate, clinofibrate, clofibrate, clofibric acid, ezetimibe, etofibrate, fenofibrate, fenofibric acid, gemfibrozil, niacin, nicofibrate, pirifibrate, probucol, ronifibrate, simfibrate, and theofibrate; muscle relaxants including, for example and without limitation, cyclobenzaprine, dantrolene sodium and tizanidine HCl; agents to treat neurodegenerative diseases, including active drug substances for treating Alzheimer's disease including, for example and without limitation, akatinol, donezepil, donepezil hydrochloride, dronabinol, galantamine, neotrofin, rasagiline, physostigmine, physostigmine salicylate, propentoffyline, quetiapine, rivastigmine, tacrine, tacrine hydrochloride, thalidomide, and xaliproden; drug substances for treating Huntington's Disease including, for example and without limitation, fluoxetine and carbamazepine; anti-parkinsonism drugs useful such as, without limitation amantadine, apomorphine, bromocriptine, entacapone, levodopa (particularly a levodopa/carbidopa combination), lysuride, pergolide, pramipexole, rasagiline, riluzole, ropinirole, selegiline, sumanirole, tolcapone, trihexyphenidyl, and trihexyphenidyl hydrochloride; and drug substances for treating ALS such, without limitation, the anti-spastic agents baclofen, diazemine, and tizanidine; nitrates and other antianginal drug substances including, for example and without limitation, amyl nitrate, glyceryl trinitrate, isosorbide dinitrate, isosorbide mononitrate and pentaerythritol tetranitrate; neuroleptic drug substances including, for example, antidepressant drugs, antimanic drugs, and antipsychotic agents, wherein antidepressant drugs include, without limitation, (a) the tricyclic antidepressants such as amoxapine, amitriptyline, clomipramine, desipramine, doxepin, imipramine, maprotiline, nortriptyline, protriptyline, and trimipramine, (b) the serotonin reuptake inhibitors such as citalopram, fluoxetine, fluvoxamine, paroxetine, sertraline, and venlafaxine, (c) monoamine oxidase inhibitors such as phenelzine, tranylcypromine, and (−)-selegiline, and (d) other antidepressants such as apretipant, bupropion, duloxetine, gepirone, igmesine, lamotrigine, maprotiline, mianserin, mirtazapine, nefazodone, rabalzotan, sunepitron, trazodone and venlafaxine, and wherein antimanic and antipsychotic agents include, for example and without limitation, (a) phenothiazines such as acetophenazine, acetophenazine maleate, chlorpromazine, chlorpromazine hydrochloride, fluphenazine, fluphenazine hydrochloride, fluphenazine enanthate, fluphenazine decanoate, mesoridazine, mesoridazine besylate, perphenazine, thioridazine, thioridazine hydrochloride, trifluoperazine, and trifluoperazine hydrochloride, (b) thioxanthenes such as chlorprothixene, thiothixene, and thiothixene hydrochloride, and (c) other heterocyclic drugs such as carbamazepine, clozapine, droperidol, haloperidol, haloperidol decanoate, loxapine succinate, molindone, molindone hydrochloride, olanzapine, pimozide, quetiapine, risperidone, and sertindole; nutritional agents including, for example and without limitation, calcitriol, carotenes, dihydrotachysterol, essential fatty acids, non-essential fatty acids, phytonadiol, vitamin A, vitamin B.sub.2, vitamin D, vitamin E and vitamin K; opioid analgesics including, for example and without limitation, alfentanil, apomorphine, buprenorphine, butorphanol, codeine, dextropropoxyphene, diamorphine, dihydrocodeine, fentanyl, hydrocodone, hydromorphone, levorphanol, meperidine, meptazinol, methadone, morphine, nalbuphine, oxycodone, oxymorphone, pentazocine, propoxyphene, sufentanil, and tramadol; peptidyl drug substances include therapeutic peptides and proteins per se, whether naturally occurring, chemically synthesized, recombinantly produced, and/or produced by biochemical (e.g., enzymatic) fragmentation of larger molecules, and may contain the native sequence or an active fragment thereof. Specific peptidyl drugs include, for example and without limitation, the peptidyl hormones activin, amylin, angiotensin, atrial natriuretic peptide (ANP), calcitonin, calcitonin gene-related peptide, calcitonin N-terminal flanking peptide, ciliary neurotrophic factor (CNTF), corticotropin (adrenocorticotropin hormone, ACTH), corticotropin-releasing factor (CRF or CRH), epidermal growth factor (EGF), follicle-stimulating hormone (FSH), gastrin, gastrin inhibitory peptide (GIP), gastrin-releasing peptide, gonadotropin-releasing factor (GnRF or GNRH), growth hormone releasing factor (GRF, GRH), human chorionic gonadotropin (hCH), inhibin A, inhibin B, insulin, luteinizing hormone (LH), luteinizing hormone-releasing hormone (LHRH), alpha-melanocyte-stimulating hormone, beta-melanocyte-stimulating hormone, .gamma.-melanocyte-stimulating hormone, melatonin, motilin, oxytocin (pitocin), pancreatic polypeptide, parathyroid hormone (PTH), placental lactogen, prolactin (PRL), prolactin-release inhibiting factor (PIF), prolactin-releasing factor (PRF), secretin, somatotropin (growth hormone, GH), somatostatin (SIF, growth hormone-release inhibiting factor, GIF), thyrotropin (thyroid-stimulating hormone, TSH), thyrotropin-releasing factor (TRH or TRF), thyroxine, vasoactive intestinal peptide (VIP),and vasopressin. Other peptidyl drug substances are the cytokines, e.g., colony stimulating factor 4, heparin binding neurotrophic factor (HBNF), interferon-.alpha., interferon.alpha.-2a, interferon.alpha.-2b, interferon.alpha.-n3, interferon-.beta., etc., interleukin-1, interleukin-2, interleukin-3, interleukin-4, interleukin-5, interleukin-6, etc., tumor necrosis factor, tumor necrosis factor-.alpha., granuloycte colony-stimulating factor (G-CSF), granulocyte-macrophage colony-stimulating factor (GM-CSF), macrophage colony-stimulating factor, midkine (MD), and thymopoietin. Still other peptidyl drug substances include endorphins (e.g., dermorphin, dynorphin, .alpha.-endorphin, .beta.-endorphin, .gamma.-endorphin, .sigma.-endorphin, [Leu.sup.5]enkephalin, [Met.sup.5]enkephalin, substance P), kinins (e.g., bradykinin, potentiator B, bradykinin potentiator C, kallidin), LHRH analogues (e.g., buserelin, deslorelin, fertirelin, goserelin, histrelin, leuprolide, lutrelin, nafarelin, tryptorelin), and the coagulation factors, such as alpha$_1$-antitrypsin, alpha$_2$-macroglobulin, antithrombin III, factor I (fibrinogen), factor II (prothrombin), factor III (tissue prothrombin), factor V (proaccelerin), factor VII (proconvertin), factor VIII (antihemophilic globulin or AHG), factor IX (Christmas factor, plasma thromboplastin component or PTC), factor X (Stuart-Power factor), factor X1 (plasma thromboplastin antecedent or PTA), factor XII (Hageman factor), heparin cofactor II, kallikrein, plasmin, plasminogen, prekallikrein, protein C, protein S, and thrombomodulin; sex hormones include, for example and without limitation, progestins (progestogens), estrogens, and combinations thereof. Progestins include acetoxypregnenolone, allylestrenol, anagestone acetate, chlormadinone acetate, cyproterone, cyproterone acetate, desogestrel, dihydrogesterone, dimethisterone, ethisterone (17-alpha-ethinyltestosterone), ethynodiol diacetate, flurogestone acetate, gestadene, hydroxyprogesterone, hydroxyprogesterone acetate, hydroxyprogesterone caproate, hydroxymethylprogesterone, hydroxymethylprogesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, progesterone, and trimgestone. Also included within this general class are estrogens, e.g.: estradiol (i.e., 1,3, 5-estratriene-3,17-beta-diol, or "17-beta-estradiol") and its esters, including estradiol benzoate, valerate, cypionate, heptanoate, decanoate, acetate and diacetate; 17.alpha.-estradiol; ethinylestradiol (i.e., 17.alpha.-ethinylestradiol) and esters and ethers thereof, including ethinylestradiol 3-acetate and ethinylestradiol 3-benzoate; estriol and estriol succinate; polyestrol phosphate; estrone and its esters and derivatives, including estrone acetate, estrone sulfate, and piperazine estrone sulfate; quinestrol; mestranol; and conjugated equine estrogens. In many contexts, e.g., in female contraception and in hormone replacement therapy (HRT), a combination of a progestin and estrogen is used, e.g., progesterone and 17.beta.-estradiol. For HRT, an androgenic agent may be advantageously included as well. Androgenic agents for this purpose include, for example, dehydroepiandrosterone (DHEA; also termed "prasterone"), sodium dehydroepiandrosterone sulfate, 4-dihydrotestosterone (DHT; also termed "stanolone"), and testosterone, and pharmaceutically acceptable esters of testosterone and 4-dihydrotestosterone, typically esters formed from the hydroxyl group present at the C-17 position, including, but not limited to, the enanthate, propionate, cypionate, phenylacetate, acetate, isobutyrate, buciclate, heptanoate, decanoate, undecanoate, caprate and isocaprate esters; androgenic drug substances may also be administered for other purposes well known in the art. In addition to the androgenic agents enumerated above, other androgenic agents include, but are not limited to, androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, ethylestrenol, oxandrolone, nandrolone phenpropionate, nandrolone decanoate, nandrolone furylpropionate, nandrolone cyclohexane-propionate, nandrolone benzoate, nandrolone cyclohexanecarboxylate, stanozolol, dromostanolone, and dromostanolone propionate; stimulants, including active drug substances for treating narcolepsy including attention deficit disorder (ADD) and attention deficit hyperactivity disorder (ADHD) including, for example and without limitation, amphetamine, dexamphetamine, dexfenfluramine, mazindol, methylphenidate (including d-threo-methylphenidate or "dexmethylphenidate", mondafinil, pemoline and sibutramine.

Considering solubility, exemplary hydrophobic active agents include, without limitation, acetretin, acetyl coenzyme Q., albendazole, albuterol, aminoglutethimide, amiodarone, amlodipine, amphetamine, amphotericin B, atorvastatin, atovaquone, azithromycin, baclofen, beclomethasone, benazepril, benzonatate, betamethasone, bicalutanide, budesonide, bupropion, busulfan, butenafine, calcifediol, calcipotriene, calcitriol, camptothecin, candesartan, capsaicin, carbamezepine, carotenes, celecoxib, cerivastatin, cetirizine, chlorpheniramine, cholecalciferol, cilostazol, cimetidine, cinnarizine, ciprofloxacin, cisapride, clarithromycin, clemastine, clomiphene, clomipramine, clopidogrel, codeine, coenzyme Q1O, cyclobenzaprine, cyclosporin, danazol, dantrolene, dexchlorpheniramine, diclofenac, dicumarol, digoxin, dehydroepiandrosterone, dihydroergotamine, dihydrotachysterol, dirithromycin, donezepil, efavirenz, eposartan, ergocalciferol, ergotamine, essential fatty acid sources, estradiol, etodolac, etoposide, famotidine, fenofibrate, fentanyl, fexofenadine, finasteride, fluconazole, flurbiprofen, fluvastatin, fosphenytoin, frovatriptan, furazolidone, gabapentin, gemfibrozil, glibenclamide, glipizide, glyburide, glimepiride, griseofulvin, halofantrine, ibuprofen, irbesartan, irinotecan, isosorbide dinitrate, isotretinoin, itraconazole, ivermectin, ketoconazole, ketorolac, lamotrigine, lansoprazole, leflunomide, lisinopril, loperamide, loratadine, lovastatin, L-thyroxine, lutein, lycopene, medroxyprogesterone, mifepristone, mefloquine, megestrol acetate, methadone, methoxsalen, metronidazole, miconazole, midazolam, miglitol, minoxidil, mitoxantrone, montelukast, nabumetone, nalbuphine, naratriptan, nelfinavir, nifedipine, nisoldipine, nilutanide, nitro furantoin, nizatidine, omeprazole, oprevelkin, oxaprozin, paclitaxel, paracalcitol, paroxetine, pentazocine, pioglitazone, pizofetin, pravastatin, prednisolone, probucol, progesterone, pseudoephedrine, pyridostigmine, rabeprazole, raloxifene, repaglinide, rifabutine, rifapentine, rimexolone, ritanovir, rizatriptan, rofecoxib, rosiglitazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terazosin, tetrahydrocannabinol, tiagabine, ticlopidine, tirofiban, tizanidine, topiramate, topotecan, toremifene, tramadol, tretinoin, troglitazone, trovafloxacin, ubidecarenone, valsartan, venlafaxine, verteporfin, vigabatrin, vitamin A, vitamin D, vitamin E, vitamin K, zafirlukast, zileuton, zolmitriptan, Zolpidem, zopiclone, and combinations thereof.

Exemplary hydrophilic active agents include, without limitation, acarbose, acyclovir, acetyl cysteine, acetylcholine chloride, alatrofloxacin, alendronate, alglucerase, amantadine hydrochloride, ambenomium, amifostine, amiloride hydrochloride, aminocaproic acid, amphotericin B, antihemophilic factor (human), antihemophilic factor (porcine), antihemophilic factor (recombinant), aprotinin, asparaginase, atenolol, atracurium besylate, atropine, azithromycin, aztreonam, BCG vaccine, bacitracin, becaplermin, belladona, bepridil hydrochloride, bleomycin sulfate, calcitonin human, calcitonin salmon, carboplatin, capecitabine, capreomycin sulfate, cefamandole nafate, cefazolin sodium, cefepime hydrochloride, cefixime, cefonicid sodium, cefoperazone, cefotetan disodium, cefotaxime, cefoxitin sodium, ceftizoxime, ceftriaxone, cefuroxime axetil, cephalexin, cephapirin sodium, cholera vaccine, chorionic gonadotropin, cidofovir, cisplatin, cladribine, clidinium bromide, clindamycin and clindamycin derivatives, ciprofloxacin, clodronate, colistimethate sodium, colistin sulfate, corticotropin, cosyntropin, cromolyn sodium, cytarabine, dalteparin sodium, danaparoid, deferoxamine, denileukin diftitox, desmopressin, diatrizoate meglumine and diatrizoate sodium, dicyclomine, didanosine, dirithromycin, dopamine hydrochloride, dornase alpha, doxacurium chloride, doxorubicin, etidronate disodium, enalaprilat, enkephalin, enoxaparin, enoxaprin sodium, ephedrine, epinephrine, epoetin alpha, erythromycin, esmolol hydrochloride, factor IX, famciclovir, fludarabine, fluoxetine, foscarnet sodium, ganciclovir, granulocyte colony stimulating factor, granulocyte-macrophage stimulating factor, recombinant human growth hormone, bovine growth hormone, gentamycin, glucagon, glycopyrolate, gonadotropin releasing hormone and synthetic analogs thereof, gonadorelin, grepafloxacin, haemophilus B conjugate vaccine, hepatitis A virus vaccine inactivated, hepatitis B virus vaccine inactivated, heparin sodium, indinavir sulfate, influenza virus vaccine, interleukin-2, interleukin-3, insulin-human, insulin lispro, insulin procine, insulin NPH, insulin aspart, insulin glargine, insulin detemir, interferon alpha, interferon beta, ipratropium bromide, ifosfamide, Japanese encephalitis virus vaccine, lamivudine, leucovorin calcium, leuprolide acetate, levofloxacin, lincomycin and lincomycin derivatives, lobucavir, lomefloxacin, loracarbef, mannitol, measles virus vaccine, meningococcal vaccine, menotropins, mepenzolate bromide, mesalamine, methenamine, methotrexate, methscopolamine, metformin hydrochloride, metoprolol, mezlocillin sodium, mivacurium chloride, mumps viral vaccine, nedocromil sodium, neostigmine bromide, neostigmine methyl sulfate, neurontin, norfloxacin, octreotide acetate, ofloxacin, olpadronate, oxytocin, pamidronate disodium, pancuronium bromide, paroxetine, perfloxacin, pentamidine isethionate, pentostatin, pentoxifylline, penciclovir, pentagastrin, phentolamine mesylate, phenylalanine, physostigmine salicylate, plague vaccine, piperacillin sodium, platelet derived growth factor, pneumococcal vaccine polyvalent, poliovirus vaccine (inactivated), poliovirus vaccine live (OPV), polymyxin B sulfate, pralidoxime chloride, pramlintide, pregabalin, propafenone, propenthaline bromide, pyridostigmine bromide, rabies vaccine, risedronate, ribavirin, rimantadine hydrochloride, rotavirus vaccine, salmeterol xinafoate, sincalide, small pox vaccine, solatol, somatostatin, sparfloxacin, spectinomycin, stavudine, streptokinase, streptozocin, suxamethonium chloride, tacrine hydrochloride, terbutaline sulfate, thiopeta, ticarcillin, tiludronate, timolol, tissue type plasminogen activator, TNFR:Fc, TNK-tPA, trandolapril, trimetrexate gluconate, trospectomycin, trovafloxacin, tubocurarine chloride, tumor necrosis factor, typhoid vaccine live, urea, urokinase, vancomycin, valacyclovir, valsartan, varicella virus vaccine live, vasopressin and vasopressin derivatives, vecuronium bromide, vinblastine, vincristine, vinorelbine, vitamin B12, warfarin sodium, yellow fever vaccine, zalcitabine, zanamivir, zolendronate, zidovudine, and combinations thereof.

Of course, certain active agents indicated as hydrophobic may be readily converted to and commercially available in hydrophilic form, e.g., by ionizing a non-ionized active agent so as to form a pharmaceutically acceptable, pharmacologically active salt. Conversely, certain active agents indicated as hydrophilic may be readily converted to and commercially available in hydrophobic form, e.g., by neutralization, esterification, or the like. Thus, it should be understood that the above categorization of certain active agents as hydrophilic or hydrophobic is not intended to be limiting.

Any of the aforementioned active agents may also be administered in combination using the present formulations. Active agents administered in combination may be from the same therapeutic class (e.g., lipid-regulating agents or anticoagulants) or from different therapeutic classes (e.g., a lipid-regulating agent and an anticoagulant). Non-limiting examples of drug substance combination products include, without limitation: female contraceptive compositions containing both a progestogen and an estrogen; female HRT compositions containing a progestogen, an estrogen, and an androgen; combinations of lipid-regulating agents, e.g., (a) a fibrate and a statin, such as fenofibrate and atorvastatin, fenofibrate and simvastatin, fenofibrate and lovastatin, or fenofibrate and pravastatin; (b) a fibrate and nicotinic acid, such fenofibrate and niacin; and (c) a statin and a nicotinic acid, such as lovastatin and niacin; combinations of a lipid-regulating agent and an antiviral agent, e.g., a fibrate and a protease inhibitor, such as fenofibrate and ritonavir; combinations of a lipid-regulating agent and an anticoagulant, e.g., (a) a fibrate and a salicylate, such as fenofibrate and aspirin, (b) a fibrate and another anticoagulant, such as fenofibrate and clopidogrel, (c) a statin and a salicylate, such as simvastatin and aspirin, and (d) a statin and another anticoagulant such as pravastatin and clopidogrel; combinations of a lipid-regulating agent and an antidiabetic agent, including (a) a fibrate and a insulin sensitizer such as a thiazolidinedione, e.g., fenofibrate and pioglitazone, or fenofibrate and rosiglitazone, (b) a fibrate and an insulin stimulant such as a sulfonylurea, e.g., fenofibrate and glimepiride, or fenofibrate and glipizide, a statin and an insulin sensitizer such as a thiazolidinedione, e.g., lovastatin and pioglitazone, simvastatin and rosiglitazone, pravastatin and pioglitazone, or the like; combinations of a lipid regulating agent and a cardiovascular drug, e.g., (a) a fibrate and a calcium channel blocker, such as fenofibrate and amlodipine, or fenofibrate and irbesartan, or (b) a statin and a calcium channel blocker, such as fosinopril and pravastatin; combinations of anticoagulants, e.g., (a) a salicylate and a platelet receptor binding inhibitor, such as aspirin and clopidogrel, (b) a salicylate and a low molecular weight heparin, such as aspirin and dalteparin, and (c) a platelet receptor binding inhibitor and a low molecular weight heparin, such as clopidogrel and enoxaparin; combinations of antidiabetics, e.g., (a) an insulin sensitizer and an insulin stimulant, such as (i) a thiazolidinedione such as glitazone or pioglitazone and a sulfonylurea such as glimepiride, and (ii) a biguanide such as metformin and a meglitinide such as repaglinide, (b) an insulin sensitizer and an .alpha.-glucosidase inhibitor, such as metformin and acarbose, (c) an insulin stimulant and an .alpha.-glucosidase inhibitor, such as (i) a sulfonylurea such as glyburide combined with acarbose, (ii) acarbose and a meglitinide such as repaglinide, (iii) miglitol and a sulfonylurea such as glipizide, (iv) acarbose and a thiazolidinedione such as pioglitazone, or (v) metformin and pioglitazone; combinations of cardiovascular drugs, such as combinations of ACE inhibitors, e.g., lisinopril and candesartan; a combination of an ACE inhibitor with a diuretic agent such as losartan and hydrochlorothiazide; a combination of a calcium channel blocker and a .beta.-blocker such as nifedipine and atenolol; and a combination of a calcium channel blocker and an ACE inhibitor such as felodipine and ramipril; combinations of an antihypertensive agent and an antidiabetic agent, such as an ACE inhibitor and a sulfonylurea, e.g., irbesartan and glipizide; combinations of antihistamines and antiasthmatic agents, e.g., an antihistamine and a leukotriene receptor antagonist such as loratadine and zafirlukast, desloratidine and zafirlukast, and cetirazine and montelukast; combinations of antiinflammatory agents and analgesics, e.g., a COX-2 inhibitor and a nonsteroidal antiinflammatory agent (NSAID) such as rofecoxib and naproxen, or a COX-2 inhibitor and a salicylate such as celecoxib and aspirin; combinations of an anti-obesity drug and an antidiabetic agent, e.g., a lipase inhibitor such as orlistat in combination with metformin; combinations of a lipid-regulating agent and a drug for treating coronary artery disease, e.g., fenofibrate and ezetimibe, or lovastatin and ezetimibe; and other combinations, such as docetaxel and cisplatin, tirapazamine and cisplatin, metoclopramide and naproxen sodium, an opioid analgesic such as oxycodone and an antiinflammatory agent, an agent for treating erectile dysfunction, such as alprostadil, with an antihypertensive/vasodilator such as prazosin.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a subject may also be determined, as can the temporal requirements for administering each agent to provide a detectable therapeutic benefit to the subject. Accordingly, while certain dose and administration regimens are exemplified herein, these examples in no way limit the dose and administration regimen that may be provided to a subject in practicing the present disclosure.

It is to be noted that dosage values may vary with the type and severity of the condition to be ameliorated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this disclosure may be based on a variety of factors, including the type of disease, the age, weight, sex, medical condition of the subject, the severity of the condition, the route of administration, and the particular peptide employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present disclosure encompasses intra-subject dose-escalation as determined by the skilled artisan. Determining appropriate dosages and regimens are well-known in the relevant art and would be understood to be encompassed by the skilled artisan once provided the teachings disclosed herein.

The dose of the peptide of the present disclosure also will be determined by the existence, nature and extent of any adverse side effects that might accompany the administration of a particular peptide of the present disclosure. Typically, the attending physician will decide the dosage of the peptide of the present disclosure with which to treat each individual patient, taking into consideration a variety of factors, such as age, body weight, general health, diet, sex, peptide of the present disclosure to be administered, route of administration, and the severity of the condition being treated. By way of example and not intending to be limiting, the dose of the peptide of the present disclosure can be about 0.0001 to about 100 mg/kg body weight of the subject being treated/day, from about 0.001 to about 10 mg/kg body weight/day, or about 0.01 mg to about 1 mg/kg body weight/day. The peptide can be administered in one or more doses, such as from 1 to 3 doses per day.

In various embodiments, single or multiple administrations of the pharmaceutical compositions are administered depending on the dosage and frequency as required and tolerated by the subject. In any event, the composition should provide a sufficient quantity of at least one of the peptide disclosed herein to effectively treat the subject. The dosage can be administered once but may be applied periodically until either a therapeutic result is achieved or until side effects warrant discontinuation of therapy.

The dosing frequency of the administration of the peptide pharmaceutical composition depends on the nature of the therapy and the particular disease being treated. The administration may be once, twice, three times or four times daily, for the peptide. Treatment of a subject with a therapeutically effective amount of a peptide, can include a single treatment or, preferably, can include a series of treatments. In a preferred example, a subject is treated with peptide daily, one time per week or biweekly.

Peptides can be prepared as described in US Provisional Application No. 62/401,123 and in International Patent Application No. PCT/US2017/053597, filed 27 Sep. 2017, published as WO 2018/064098 on 5 Apr. 2018, incorporated herein by reference.

For example, in addition to being overweight or obese, a subject or patient can further have overweight- or obesity-related comorbidities, i.e., diseases and other adverse health conditions associated with, exacerbated by, or precipitated by being overweight or obese. Contemplated herein are disclosed peptide formulations of the current invention administered alone in combination with at least one other agent that has previously been shown to treat these overweight- or obesity-related conditions.

For example, Type II diabetes has been associated with obesity. Certain complications of Type II diabetes, e.g., disability and premature death, can be prevented, ameliorated, or eliminated by sustained weight loss (Astrup, A. Pub Health Nutr (2001) 4:499-5 15). Agents administered to treat Type II diabetes include sulfonylureas (e.g., Chlorpropamide, Glipizide, Glyburide, Glimepiride); meglitinides (e.g., Repaglinide and Nateglinide); biguanides (e.g., Metformin); thiazolidinediones (Rosiglitazone, Troglitazone, and Pioglitazone); dipeptidylpeptidase-4 inhibitors (e.g., Sitagliptin, Vildagliptin, and Saxagliptin); glucagon-like peptide-1 mimetics (e.g., Exenatide and Liraglutide); and alpha-glucosidase inhibitors (e.g., Acarbose and Miglitol.

Cardiac disorders and conditions, for example hypertension, dyslipidemia, ischemic heart disease, cardiomyopathy, cardiac infarction, stroke, venous thromboembolic disease and pulmonary hypertension, have been linked to overweight or obesity. For example, hypertension has been linked to obesity because excess adipose tissue secretes substances that are acted on by the kidneys, resulting in hypertension. Additionally, with obesity there are generally higher amounts of insulin produced (because of the excess adipose tissue) and this excess insulin also elevates blood pressure. A major treatment option of hypertension is weight loss. Agents administered to treat hypertension include Chlorthalidone; Hydrochlorothiazide; Indapamide, Metolazone; loop diuretics (e.g., Bumetanide, Ethacrynic acid, Furosemide, Lasix, Torsemide); potassium-sparing agents (e.g., Amiloride hydrochloride, benzamil, Spironolactone, and Triamterene); peripheral agents (e.g., Reserpine); central alpha-agonists (e.g., Clonidine hydrochloride, Guanabenz acetate, Guanfacine hydrochloride, and Methyldopa); alpha-blockers (e.g., Doxazosin mesylate, Prazosin hydrochloride, and Terazosin hydrochloride); beta-blockers (e.g., Acebutolol, Atenolol, Betaxolol, Bisoprolol fumarate, Carteolol hydrochloride, Metoprolol tartrate, Metoprolol succinate, Nadolol, Penbutolol sulfate, Pindolol, Propranolol hydrochloride, and Timolol maleate); combined alpha- and beta-blockers (e.g., Carvedilol and Labetalol hydrochloride); direct vasodilators (e.g., Hydralazine hydrochloride and Minoxidil); calcium antagonists (e.g., Diltiazem hydrochloride and Verapamil hydrochloride); dihydropyridines (e.g., Amlodipine besylate, Felodipine, Isradipine, Nicardipine, Nifedipine, and Nisoldipine); ACE inhibitors (benazepril hydrochloride, Captopril, Enalapril maleate, Fosinopril sodium, Lisinopril, Moexipril, Quinapril hydrochloride, Ramipril, Trandolapril); Angiotensin II receptor blockers (e.g., Losartan potassium, Valsartan, and Irbesartan); Renin inhibitors (e.g., Aliskiren); and combinations thereof. These compounds are administered in regimens and at dosages known in the art.

Carr et al. (The Journal of Clinical Endocrinology & Metabolism (2004) Vol. 89, No. 6 2601-2607) discusses a link between being overweight or obese and dyslipidemia. Dyslipidemia is typically treated with statins. Statins, HMG-CoA reductase inhibitors, slow down production of cholesterol in a subject and/or remove cholesterol buildup from arteries. Statins include mevastatin, lovastatin, pravastatin, simvastatin, velostatin, dihydrocompactin, fluvastatin, atorvastatin, dalvastatin, carvastatin, crilvastatin, bevastatin, cefvastatin, rosuvastatin, pitavastatin, and glenvastatin. These compounds are administered in regimens and at dosages known in the art. Eckel (Circulation (1997) 96:3248-3250) discusses a link between being overweight or obese and ischemic heart disease. Agents administered to treat ischemic heart disease include statins, nitrates (e.g., Isosorbide Dinitrate and Isosorbide Mononitrate), beta-blockers, and calcium channel antagonists. These compounds are administered in regimens and at dosages known in the art.

Wong et al. (Nature Clinical Practice Cardiovascular Medicine (2007) 4:436-443) discusses a link between being overweight or obese and cardiomyopathy. Agents administered to treat cardiomyopathy include inotropic agents (e.g., Digoxin), diuretics (e.g., Furosemide), ACE inhibitors, calcium antagonists, anti-arrhythmic agents (e.g., Sotolol, Amiodarone and Disopyramide), and beta-blockers. These compounds are administered in regimens and at dosages known in the art. Yusef et al. (Lancet (2005) 366(9497): 1640-1649) discusses a link between being overweight or obese and cardiac infarction. Agents administered to treat cardiac infarction include ACE inhibitors, Angiotensin II receptor blockers, direct vasodilators, beta blockers, anti-arrhythmic agents and thrombolytic agents (e.g., Alteplase, Retaplase, Tenecteplase, Anistreplase, and Urokinase). These compounds are administered in regimens and at dosages known in the art.

Suk et al. (Stroke (2003) 34: 1586-1592) discusses a link between being overweight or obese and strokes. Agents administered to treat strokes include anti-platelet agents (e.g., Aspirin, Clopidogrel, Dipyridamole, and Ticlopidine), anticoagulant agents (e.g., Heparin), and thrombolytic agents. Stein et al. (The American Journal of Medicine (2005) 18(9):978-980) discusses a link between being overweight or obese and venous thromboembolic disease. Agents administered to treat venous thromboembolic disease include anti-platelet agents, anticoagulant agents, and thrombolytic agents. Sztrymf et al. (Rev Pneumol Clin (2002) 58(2): 104-10) discusses a link between being overweight or obese and pulmonary hypertension. Agents administered to treat pulmonary hypertension include inotropic agents, anticoagulant agents, diuretics, potassium (e.g., K-dur), vasodilators (e.g., Nifedipine and Diltiazem), Bosentan, Epoprostenol, and Sildenafil. Respiratory disorders and conditions such as obesity-hypoventilation syndrome, asthma, and obstructive sleep apnea, have been linked to being overweight or obese. Elamin (Chest (2004) 125: 1972-1974) discusses a link between being overweight or obese and asthma. Agents administered to treat asthma include bronchodilators, anti-inflammatory agents, leukotriene blockers, and anti-Ige agents. Particular asthma agents include Zafirlukast, Flunisolide, Triamcinolone, Beclomethasone, Terbutaline, Fluticasone, Formoterol, Beclomethasone, Salmeterol, Theophylline, and Xopenex.

Kessler et al. (Eur Respir J (1996) 9:787-794) discusses a link between being overweight or obese and obstructive sleep apnea. Agents administered to treat sleep apnea include Modafinil and amphetamines.

Hepatic disorders and conditions, such as nonalcoholic fatty liver disease, have been linked to being overweight or obese. Tolman et al. (Ther Clin Risk Manag (2007) 6: 1153-1163) discusses a link between being overweight or obese and nonalcoholic fatty liver disease. Agents administered to treat nonalcoholic fatty liver disease include antioxidants (e.g., Vitamins E and C), insulin sensitizers (Metformin, Pioglitazone, Rosiglitazone, and Betaine), hepatoprotectants, and lipid-lowering agents.

Skeletal disorders and conditions, such as, back pain and osteoarthritis of weight-bearing joints, have been linked to being overweight or obese, van Saase (J Rheumatol (1988) 15(7): 1152-1158) discusses a link between being overweight or obese and osteoarthritis of weight-bearing joints. Agents administered to treat osteoarthritis of weight-bearing joints include Acetaminophen, non-steroidal anti-inflammatory agents (e.g., Ibuprofen, Etodolac, Oxaprozin, Naproxen, Diclofenac, and Nabumetone), COX-2 inhibitors (e.g., Celecoxib), steroids, supplements (e.g. glucosamine and chondroitin sulfate), and artificial joint fluid.

Metabolic disorders and conditions, for example, Prader-Willi Syndrome and polycystic ovary syndrome, have been linked to being overweight or obese. Cassidy (Journal of Medical Genetics (1997) 34:917-923) discusses a link between being overweight or obese and Prader-Willi Syndrome. Agents administered to treat Prader-Willi Syndrome include human growth hormone (HGH), somatropin, and weight loss agents (e.g., Orlistat, Sibutramine, Methamphetamine, Ionamin, Phentermine, Bupropion, Diethylpropion, Phendimetrazine, Benzphetermine, and Topamax).

Hoeger (Obstetrics and Gynecology Clinics of North America (2001) 28(1):85-97) discusses a link between being overweight or obese and polycystic ovary syndrome. Agents administered to treat polycystic ovary syndrome include insulin-sensitizers, combinations of synthetic estrogen and progesterone, Spironolactone, Eflornithine, and Clomiphene. Reproductive disorders and conditions such as sexual dysfunction, erectile dysfunction, infertility, obstetric complications, and fetal abnormalities, have been linked to being overweight or obese. Larsen et al. (Int J Obes (Lond) (2007) 8: 1189-1198) discusses a link between being overweight or obese and sexual dysfunction. Chung et al. (Eur Urol (1999) 36(1):68-70) discusses a link between being overweight or obese and erectile dysfunction. Agents administered to treat erectile dysfunction include phosphodiesterase inhibitors (e.g., Tadalafil, Sildenafil citrate, and Vardenafil), prostaglandin E analogs (e.g., Alprostadil), alkaloids (e.g., Yohimbine), and testosterone. Pasquali et al. (Hum Reprod (1997) 1:82-87) discusses a link between being overweight or obese and infertility. Agents administered to treat infertility include Clomiphene, Clomiphene citrate, Bromocriptine, Gonadotropin-releasing Hormone (GnRH), GnRH agonist, GnRH antagonist, Tamoxifen/nolvadex, gonadotropins, Human Chorionic Gonadotropin (HCG), Human Menopausal Gonadotropin (HmG), progesterone, recombinant follicle stimulating hormone (FSH), UrofoUitropin, Heparin, Follitropin alfa, and Follitropin beta.

Weiss et al. (American Journal of Obstetrics and Gynecology (2004) 190(4): 1091-1097) discusses a link between being overweight or obese and obstetric complications. Agents administered to treat obstetric complications include Bupivacaine hydrochloride, Dinoprostone PGE2, Meperidine HC1, Ferro-folic-500/iberet-folic-500, Meperidine, Methylergonovine maleate, Ropivacaine HC1, Nalbuphine HC1, Oxymorphone HC1, Oxytocin, Dinoprostone, Ritodrine, Scopolamine hydrobromide, Sufentanil citrate, and Oxytocic.

Psychiatric disorders and conditions, for example, weight-associated depression and anxiety, have been linked to being overweight or obese. Dixson et al. (Arch Intern Med (2003) 163:2058-2065) discusses a link between being overweight or obese and depression. Agents administered to treat depression include serotonin reuptake inhibitors (e.g., Fluoxetine, Escitalopram, Citalopram, Paroxetine, Sertraline, and Venlafaxine); tricyclic antidepressants (e.g., Amitriptyline, Amoxapine, Clomipramine, Desipramine, Dosulepin hydrochloride, Doxepin, Imipramine, Iprindole, Lofepramine, Nortriptyline, Opipramol, Protriptyline, and Trimipramine); monoamine oxidase inhibitors (e.g., Isocarboxazid, Moclobemide, Phenelzine, Tranylcypromine, Selegiline, Rasagiline, Nialamide, Iproniazid, Iproclozide, Toloxatone, Linezolid, Dienolide kavapyrone desmethoxyyangonin, and Dextroamphetamine); psychostimulants (e.g., Amphetamine, Methamphetamine, Methylphenidate, and Arecoline); antipsychotics (e.g., Butyrophenones, Phenothiazines, Thioxanthenes, Clozapine, Olanzapine, Risperidone, Quetiapine, Ziprasidone, Amisulpride, Paliperidone, Symbyax, Tetrabenazine, and Cannabidiol); and mood stabilizers (e.g., Lithium carbonate, Valproic acid, Divalproex sodium, Sodium valproate, Lamotrigine, Carbamazepine, Gabapentin, Oxcarbazepine, and Topiramate).

Simon et al. (Archives of General Psychiatry (2006) 63(7):824-830) discusses a link between being overweight or obese and anxiety. Agents administered to treat anxiety include serotonin reuptake inhibitors, mood stabilizers, benzodiazepines (e.g., Alprazolam, Clonazepam, Diazepam, and Lorazepam), tricyclic antidepressants, monoamine oxidase inhibitors, and beta-blockers.

Another embodiment of the invention provides methods for facilitating and maintaining weight loss in a subject involving administering to the subject an amount of a disclosed peptide formulation effective to result in weight loss in the subject; and administering a therapeutically effective amount of a different weight loss agent to maintain a reduced weight in the subject. Weight loss agents include serotonin and noradrenergic re-uptake inhibitors; noradrenergic re-uptake inhibitors; selective serotonin re-uptake inhibitors; and intestinal lipase inhibitors. Particular weight loss agents include liraglutide, orlistat, sibutramine, methamphetamine, ionamin, phentermine, bupropion, diethylpropion, phendimetrazine, benzphetermine, bromocriptine, lorcaserin, topiramate, or agents acting to modulate food intake by blocking ghrelin action, inhibiting diacylglycerol acyltransferase 1 (DGAT1) activity, inhibiting stearoyl Co A desaturase 1 (SCD1) activity, inhibiting neuropeptide Y receptor 1 function, activating neuropeptide Y receptor 2 or 4 function, or inhibiting activity of sodium-glucose cotransporters 1 or 2. These compounds are administered in regimens and at dosages known in the art.

The data presented herein and/or in in International Patent Application No. PCT/US2017/053597, filed 27 Sep. 2017, published as WO 2018/064098 on 5 Apr. 2018, incorporated herein by reference, demonstrate the ability of the presently disclosed peptides to decrease free fatty acid levels in adipocytes and support the use of such peptides for decreasing body weight, blood glucose levels, and/or fat mass in mammals in need thereof. The data presented also demonstrate the stability of such peptides in plasma and support their use as therapeutic peptides suitable for administration to mammals. Accordingly, the present disclosure provides methods of treating diseases relating to body weight, blood glucose levels, and fat mass, e.g., metabolic diseases, including obesity, fatty liver disease, and diabetes.

Without being bound by a specific theory, free fatty acids (FFA) in cell culture media after treatment of adipocytes with the peptides indicates a modulation of pathways involved in cellular regulation of lipid or fatty acid levels. Decreases in fatty acid levels in the media may result from a number of processes, including but not limited to inhibition of signaling pathways, reduction in cellular lipogenesis, reduction in lipolysis, or increase in fatty acid oxidation. Peptides that have an effect on the net concentration of free fatty acids have potential utility for treatment of metabolic disorders. The present disclosure accordingly provides a method of modulating fatty acid metabolism in a subject in need thereof, comprising administering to the subject a peptide formulation of the present disclosure in an amount effective to modulate fatty acid metabolism. In exemplary embodiments, the method is a method of increasing fatty acid metabolism in a subject in need thereof. The present disclosure also provides a method of modulating fatty acid metabolism in a cell, comprising contacting the cell with a peptide formulated as described herein, in an amount effective to modulate fatty acid metabolism. In exemplary embodiments, the method is a method of increasing fatty acid metabolism in a cell.

Lipodystrophy is a common name for disorders characterized by selective loss of adipose tissue (body fat) from various body regions and/or accumulation of excess fat in other areas. Localized fat loss from one area, such as the face, is called lipoatrophy. The extent of fat loss can range from very small areas on one part of the body to near total absence of adipose tissue from the entire body. In addition, patients may have either severe metabolic complications or mere cosmetic problems. Lipodystrophy associated with severe fat loss may contribute to metabolic complications related to insulin resistance, such as diabetes mellitus, high levels of serum triglycerides and fatty liver (hepatic steatosis). Lipodystrophy may be either congenital (such as familial partial lipodystrophy or Beradinelli-Seip syndrome) or acquired (e.g. associated with various types of illnesses or drugs). Acquired lipodystrophies are caused by medications, autoimmune mechanisms or may be idiopathic. Acquired lipodystrophies include lipodystrophy in HIV-infected patients (LD-HIV) which may be induced by highly active antiretroviral therapy (HAART), acquired generalized lipodystrophy (AGL), acquired partial lipodystrophy (APL) and localized lipodystrophy. Acquired lipodystrophies do not have a direct genetic basis. According to some embodiments, the present invention provides a method for reducing, ameliorating or preventing lipodystrophy.

The peptide formulations are useful in the treatment of conditions associated with an unbalanced metabolic state manifested by abnormal blood levels of glucose, reactive oxygen species (ROS) and/or free fatty acids (FFA). A favorable metabolic status is defined as a balanced energy homeostasis, characterized by blood levels of glucose, ROS and FFA that are equivalent to those of healthy subjects (within the range of average levels for the healthy population). Accordingly, an unfavorable metabolic status as used herein refers to blood levels of glucose, ROS and/or FFA that are abnormal, i.e. significantly altered compared to their respective levels in healthy control subjects (e.g. as evaluated by a physician or skilled artisan). The term unfavorable metabolic status refers in some embodiments to blood levels of glucose, ROS and/or FFA that are significantly enhanced compared to their respective levels in healthy control subjects (e.g. as evaluated by a physician or skilled artisan). An unfavorable metabolic status may result from abnormal metabolism which may involve glucose (carbohydrate) and/or fatty acid oxidation pathways. When aberrations in fatty acid oxidation pathways are involved, the unfavorable metabolic status is typically manifested by ROS blood levels that are significantly enhanced compared to healthy control subjects and/or by abnormal FFA blood levels. These aberrations may also be manifested by elevated blood levels of oxidized low density lipoproteins (LDL). When aberrations in glucose metabolism are involved, glucose blood levels are typically significantly enhanced compared to healthy control subjects. As used herein, a patient with significantly enhanced blood glucose levels that do not exceed the threshold for unbalanced glycemic control will be defined as having an unfavorable metabolic status if said enhancement is accompanied by abnormal blood ROS and/or FFA values, as described herein. An unbalanced metabolic state may also be evaluated by said physician or skilled artisan by considering the energy intake and various energy consumption and utilization parameters, as known in the art. For example, without limitation, parameters at the cellular level such as cellular (e.g. platelet) ATP production and cellular oxidation, and parameters at the whole body level such as respiratory quotient (RQ) may be evaluated to determine the metabolic status of the subject. For example, by comparing the relative ratio of such parameters between healthy and sick patients the skilled artisan may evaluate the metabolic status of the subject compared to healthy controls. An unfavorable metabolic status may be found in patients afflicted with chronic metabolic and/or inflammatory disorders that are not adequately treated or balanced by a suitable therapeutic regimen.

The present disclosure accordingly provides a method of treating a metabolic disease in a subject in need thereof, comprising administering to the subject a peptide formulation of the present disclosure in an amount effective to treat the metabolic disease.

The term "metabolic disease" or "metabolic disorder" refers to a group of identified disorders in which errors of metabolism, imbalances in metabolism, or sub-optimal metabolism occur, which may involve glucose (carbohydrate), fatty acid and/or protein oxidation pathways. Accordingly, when unbalanced, these disorders are typically manifested by an unfavorable metabolic status characterized by abnormal blood levels of glucose, ROS and/or FFA compared to their respective levels in healthy control subjects, as described herein. Such disorders include without limitation diabetes and disorders associated with nutritional or endocrine imbalance.

An unfavorable metabolic status may also occur as a result of chronic inflammatory disorders, in which a non-resolving, unbalanced inflammatory process is accompanied by secondary metabolic complications manifested by abnormal blood levels of glucose, ROS and/or FFA compared to their respective levels in healthy control subjects. Non-limitative examples of such disorders are sepsis and autoimmune diseases.

Syndrome X (or metabolic syndrome) denotes a set of signs and symptoms associated with the accumulation of fat in the abdomen. This form of fat distribution is common in middle-aged men and is often visible as a pot belly or paunch. Syndrome X is characterized by a number of disorders including gout, impaired glucose metabolism (increasing susceptibility to diabetes), raised blood pressure, and elevated blood cholesterol levels. People with Syndrome X have a high risk of heart disease. Syndrome X is defined as a constellation of metabolic abnormalities in serum or plasma insulin/glucose level ratios, lipids, uric acid levels, vascular physiology, and coagulation factor imbalances by the American Association of Clinical Endocrinologists. The term "syndrome X" as used herein thus refers to a condition characterized by positive diagnosis of at least two of the following: Non-insulin-dependent diabetes, blood pressure above a level considered normal, insulin level above a level considered normal, dyslipidemia, and obesity.

A peptide formulation of the present invention may be useful in the following metabolic diseases
(a) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbAlC;
(b) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;
(c) improving β-cell function, such as decreasing (β-cell apoptosis, increasing (β-cell function and/or (β-cell mass, and/or for restoring glucose sensitivity to (β-cells;
(d) prevention and/or treatment of cognitive disorders and/or neurodegenerative disorders, such as Alzheimer's disease, Parkinson's disease, and/or multiple sclerosis;
(e) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;
(f) prevention and/or treatment of diabetic complications, such as angiopathy; neuropathy, including peripheral neuropathy; nephropathy; and/or retinopathy;
(g) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo (a)) in vitro and/or in vivo;
(h) prevention and/or treatment of cardiovascular diseases, such as syndrome X, atherosclerosis, myocardial infarction, coronary heart disease, reperfusion injury, stroke, hypoxia, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atherosclerosis obliterans), diastolic dysfunction, and/or systolic dysfunction; and/or reduction of blood pressure, such as reduction of systolic blood pressure;
(i) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriatic arthritis, rheumatoid arthritis, and/or systemic lupus erythematosus;
(j) prevention and/or treatment of critical illness, such as treatment of a critically ill patient, a critical illness poly-nephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteremia, septicemia, and/or septic shock during hospitalization; and/or stabilizing blood glucose, insulin balance and optionally metabolism in intensive care unit patients with acute illness;
(k) prevention and/or treatment of polycystic ovary syndrome (PCOS);
(l) prevention and/or treatment of cerebral disease, such as cerebral ischemia, cerebral hemorrhage, and/or traumatic brain injury;
(m) prevention and/or treatment of sleep apnea;
(n) prevention and/or treatment of abuse, such as alcohol abuse and/or drug abuse;
(o) prevention or treatment of fatty liver conditions, including but not limited to Fatty Liver Disease (FLD), nonalcoholic fatty liver disease (NAFLD), and nonalcoholic steatohepatitis (NASH);
(p) treatment of intracellular production of reactive oxygen species (ROS); and/or
(q) treatment of disorders related to insulin-resistance.

In further embodiments, methods are provided herein for treating diabetes and/or diabetes related complications by administering an effective amount, of the peptide formulation to a patient in need of treatment. Advantageously, the peptides used for treating diabetes and/or related complications according to methods provided herein have anti-apoptotic activity against and/or stimulate proliferation of pancreatic β cells, such that administering the peptides increases the number of insulin producing β cells and the level of insulin produced by the patient.

The present disclosure also provides a method of treating a liver disease in a subject in need thereof, comprising administering to the subject a peptide formulation of the present disclosure in an amount effective to treat the liver disease.

In some embodiments, the disease or medical condition is Nonalcoholic fatty liver disease (NAFLD). NAFLD refers to a wide spectrum of liver disease ranging from simple fatty liver (steatosis), to nonalcoholic steatohepatitis (NASH), to cirrhosis (irreversible, advanced scarring of the liver). All of the stages of NAFLD have in common the accumulation of fat (fatty infiltration) in the liver cells (hepatocytes). Simple fatty liver is the abnormal accumulation of a certain type of fat, triglyceride, in the liver cells with no inflammation or scarring. In NASH, the fat accumulation is associated with varying degrees of inflammation (hepatitis) and scarring (fibrosis) of the liver. The inflammatory cells can destroy the liver cells (hepatocellular necrosis). In the terms "steatohepatitis" and "steatonecrosis", steato refers to fatty infiltration, hepatitis refers to inflammation in the liver, and necrosis refers to destroyed liver cells. NASH can ultimately lead to scarring of the liver (fibrosis) and then irreversible, advanced scarring (cirrhosis). Cirrhosis that is caused by NASH is the last and most severe stage in the NAFLD spectrum. (Mendler, Michel, "Fatty Liver: Nonalcoholic Fatty Liver Disease (NAFLD) and Nonalcoholic Steatohepatitis (NASH)," ed. Schoenfield, Leslie J., MedicineNet.com, Aug. 29, 2005).

Alcoholic Liver Disease, or Alcohol-Induced Liver Disease, encompasses three pathologically distinct liver diseases related to or caused by the excessive consumption of alcohol: fatty liver (steatosis), chronic or acute hepatitis, and cirrhosis. Alcoholic hepatitis can range from a mild hepatitis, with abnormal laboratory tests being the only indication of disease, to severe liver dysfunction with complications such as jaundice (yellow skin caused by bilirubin retention), hepatic encephalopathy (neurological dysfunction caused by liver failure), ascites (fluid accumulation in the abdomen), bleeding esophageal varices (varicose veins in the esophagus), abnormal blood clotting and coma. Histologically, alcoholic hepatitis has a characteristic appearance with ballooning degeneration of hepatocytes, inflammation with neutrophils and sometimes Mallory bodies (abnormal aggregations of cellular intermediate filament proteins). Cirrhosis is characterized anatomically by widespread nodules in the liver combined with fibrosis. (Worman, Howard J., "Alcoholic Liver Disease", Columbia University Medical Center website).

Without being bound to any particular theory, the peptides described herein are useful for the treatment of Alcoholic Liver Disease, NAFLD, or any stage thereof, including, for example, steatosis, steatohepatitis, hepatitis, hepatic inflammation, NASH, cirrhosis, or complications thereof. Accordingly, the present disclosures provides a method of preventing or treating Alcoholic Liver Disease, NAFLD, or any stage thereof, in a subject comprising providing to a subject a peptide formulation described herein in an amount effective to prevent or treat Alcoholic Liver Disease, NAFLD, or the stage thereof. Such treatment methods include reduction in one, two, three or more of the following: liver fat content, incidence or progression of cirrhosis, incidence of hepatocellular carcinoma, signs of inflammation, e.g.,abnormal hepatic enzyme levels (e.g., aspartate aminotransferase AST and/or alanine aminotransferase ALT, or LDH), elevated serum ferritin, elevated serum bilirubin, and/or signs of fibrosis, e.g.,elevated TGF-beta levels. In exemplary embodiments, the peptide formulation is used to treat patients who have progressed beyond simple fatty liver (steatosis) and exhibit signs of inflammation or hepatitis. Such methods may result, for example, in reduction of AST and/or ALT levels.

In some embodiments, the peptides have anticancer activity. For example, in some embodiments, the peptides have pro-apoptotic activity against cancer cells, such as but not limited to, prostate cancer cells and/or breast cancer cells. In further embodiments, the peptides have anti-proliferative activity against cancer cells, such as but not limited to, prostate cancer cells and/or breast cancer cells.

The present disclosure also provides a method of treating cancer in a subject in need thereof, comprising administering to the subject a peptide formulation of the present disclosure in an amount effective to treat the cancer. The present disclosure also includes methods of treating cancer comprising administering an effective amount of a peptide formulation to a subject in need of treatment. The peptides provided herein exert a variety of anticancer effects and can be used to treat a wide range of cancers and other proliferative disorders. Peptides provided herein can have a variety of anticancer activities, such as but not limited to, inducing apoptosis in cancerous cells, inhibiting tumor angiogenesis, inhibiting tumor metastasis, modulating the cell cycle, inhibiting cancer cell proliferation, promoting cancer cell differentiation, inhibiting production of and/or protecting against reactive oxygen species, and enhancing stress resistance. A "cancer" refers generally to a disease characterized by uncontrolled, abnormal cell growth and proliferation. A "tumor" or "neoplasm" is an abnormal mass of tissue that results from excessive, un controlled, and progressive cell division. Methods described herein are useful for treating cancers and proliferative disorders of any type, including but not limited to, carcinomas, sarcomas, soft tissue sarcomas, lymphomas, hematological cancers, leukemias, germ cell tumors, and cancers without solid tumors (e.g., hematopoietic cancers). In various embodiments, the peptides can be used to treat cancers and/or tumors originating from and/or effecting any tissue, including but not limited to, lung, breast, epithelium, large bowel, rectum, testicle, bladder, thyroid, gallbladder, bile duct, biliary tract, prostate, colon, stomach, esophagus, pancreas, liver, kidney, uterus, cervix, ovary, and brain tissues. Non-limiting examples of specific cancers treatable with the peptides include, but are not limited to, acute lymphoblastic leukemia, acute myeloid leukemia, chronic lymphocytic leukemia, chronic myelogenous leukemia, adrenocortical carcinoma, AIDS-related lymphoma, anal cancer, astrocytoma, cerebral basal cell carcinoma, bile duct cancer, extrahepatic bladder cancer, bladder cancer, bone cancer, osteosarcoma/malignant fibrous histiocytoma, brain stem glioma, brain tumor, brain stem glioma, cerebral astrocytoma/malignant glioma, ependymoma, medulloblastoma, supratentorial primitive neuroectodermal tumor, visual pathway and hypothalamic glioma, breast cancer, male bronchial adenomas/carcinoids, Burkitt's lymphoma, carcinoid tumor, gastrointestinal carcinoma of unknown primary central nervous system lymphoma, cervical cancer, chronic lymphocytic leukemia, chronic myelogenous leukemia, chronic myeloproliferative disorders, colon cancer, colorectal cancer, cutaneous t-cell lymphoma, mycosis fungoides and sezary syndrome, endometrial cancer, ependymoma, esophageal cancer, Ewing's family tumors, germ cell tumors, extrahepatic bile duct cancer, eye cancer, intraocular melanoma, retinoblastoma, gallbladder cancer, gastric (stomach) cancer, gastrointestinal carcinoid tumors, ovarian gestational, trophoblastic tumors, glioma, hypothalamic skin cancer (melanoma), skin cancer (non-melanoma), skin carcinoma, small cell lung cancer, small intestine cancer, soft tissue sarcoma, squamous cell carcinoma, squamous neck cancer with occult primary, metastatic stomach (gastric)

cancer, stomach (gastric) cancer, t-cell lymphoma, testicular cancer, thymoma, thymic carcinoma, thyroid cancer, transitional cell cancer of the renal pelvis, ureter trophoblastic tumors, transitional cell cancer, urethral cancer, uterine cancer, uterine sarcoma, vaginal cancer, hypothalamic glioma, vulvar cancer, Waldenstrom's macroglobulinemia, Wilms' tumor, hairy cell leukemia, head and neck cancer, hepatocellular (liver) cancer, Hodgkin's lymphoma, hypopharyngeal cancer, islet cell carcinoma (endocrine pancreas), Kaposi's sarcoma, kidney (renal cell) cancer, kidney cancer, laryngeal cancer, hairy cell lip and oral cavity cancer, liver cancer, lung cancer, non-small cell lung cancer, small cell lymphoma, Burkitt's lymphoma, cutaneous t-cell, Hodgkin's lymphoma, non-Hodgkin's lymphoma, Waldenstrom's malignant fibrous histiocytoma of bone/osteosarcoma medulloblastoma, intraocular (eye) merkel cell carcinoma, mesothelioma, malignant mesothelioma, metastatic squamous neck cancer with occult primary multiple endocrine neoplasia syndrome, multiple myeloma/plasma cell neoplasm, mycosis fungoides myelodysplastic syndromes, myelodysplastic/myeloproliferative diseases, myelogenous leukemia, multiple myeloproliferative disorders, chronic nasal cavity and paranasal sinus cancer, nasopharyngeal cancer, pleoropulmonary blastoma, osteosarcoma/malignant fibrous histiocytoma of bone, pheochromocytoma, pineoblastoma, and supratentorial primitive neuroectodermal tumors. In some embodiments, the cancer is breast cancer. In some embodiments, the cancer is prostate cancer.

In some embodiments, administering a peptide formulation according to a method provided herein enhances efficacy of an established cancer therapy. In further embodiments, administering a peptide formulation according to a method provided herein enhances the anticancer activity of another cancer therapy, such as radiation or chemotherapy. In some embodiments, methods are provided herein for inducing cell death in cancer cells and/or tumor cells, the methods comprising administering a peptide formulation described herein in an amount sufficient to induce cancer cell death and/or tumor cell death.

In some embodiments, the peptides have one or more cell protective or cytoprotective activities. For example, in some embodiments, the peptides are capable of preventing cell damage, improving cell survival, and/or enhancing resistance to environmental stress, such as but not limited to, heat shock, serum withdrawal, chemotherapy, and/or radiation.

In some embodiments, administering a peptide formulation according to a method provided herein decreases adverse effects of an established cancer therapy.

Further preferred medical uses include treatment or prevention of degenerative disorders, particularly neurodegenerative disorders such as Alzheimer's disease, Parkinson's disease, Huntington's disease, ataxia, e.g. spinocerebellar ataxia, Kennedy disease, myotonic dystrophy, Lewy body dementia, multi-systemic atrophy, amyotrophic lateral sclerosis, primary lateral sclerosis, spinal muscular atrophy, prion-associated diseases, e.g. Creutzfeldt-Jacob disease, multiple sclerosis, telangiectasia, Batten disease, corticobasal degeneration, corticobasal degeneration, subacute combined degeneration of spinal cord, Tabes dorsalis, Tay-Sachs disease, toxic encephalopathy, infantile Refsum disease, Refsum disease, neuroacanthocytosis, Niemann-Pick disease, Lyme disease, Machado-Joseph disease, Sandhoff disease, Shy-Drager syndrome, wobbly hedgehog syndrome, proteopathy, cerebral β-amyloid angiopathy, retinal ganglion cell degeneration in glaucoma, synucleinopathies, tauopathies, frontotemporal lobar degeneration (FTLD), dementia, cadasil syndrome, hereditary cerebral hemorrhage with amyloidosis, Alexander disease, seipinopathies, familial amyloidotic neuropathy, senile systemic amyloidosis, serpinopathies, AL (light chain) amyloidosis (primary systemic amyloidosis), AH (heavy chain) amyloidosis, AA (secondary) amyloidosis, aortic medial amyloidosis, ApoAI amyloidosis, ApoAII amyloidosis, ApoAIV amyloidosis, familial amyloidosis of the Finnish type (FAF), Lysozyme amyloidosis, Fibrinogen amyloidosis, Dialysis amyloidosis, Inclusion body myositis/myopathy, Cataracts, Retinitis pigmentosa with rhodopsin mutations, medullary thyroid carcinoma, cardiac atrial amyloidosis, pituitary prolactinoma, Hereditary lattice corneal dystrophy, Cutaneous lichen amyloidosis, Mallory bodies, corneal lactoferrin amyloidosis, pulmonary alveolar proteinosis, odontogenic (Pindborg) tumor amyloid, cystic fibrosis, sickle cell disease or critical illness myopathy (CIM). Without being limited by a particular theory, it is believed that the peptides provided herein have one or more activities capable of repairing and/or preventing neurodegenerative damage of neural cells and/or other cell types. "Neurodegenerative diseases" treatable according to methods provided herein are progressive diseases resulting in the degeneration and/or loss of neurons, for example due to neuronal cell death (apoptosis). Examples of neurodegenerative diseases include, but are not limited to, cerebral degenerative diseases (e.g., Alzheimer's disease (AD), Parkinson's disease, progressive supranuclear palsy, and Huntington's disease (HD)), and spinal degenerative disease/motor neuron degenerative diseases (e.g., amyotrophic lateral sclerosis (ALS), (SMA: Werdnig-Hoffmann disease or Kugelberg-Welander syndrome), spinocerebellar ataxia, bulbospinal muscular atrophy (BSMA; Kennedy-Alter-Sung syndrome)). A "motor neuron degenerative disease" is a neurodegenerative disease characterized by a progressive, retrograde disorder of upper and lower motor neurons that control motion in the body. In further embodiments, the peptides and compositions thereof are also effective in ameliorating conditions resulting from motor neuron degenerative disease, such as muscular atrophy, muscular weakness, bulbar palsy (muscular atrophy or weakness in the face, pharynx, and tongue, and aphasia or dysphagia caused thereby), muscular fasciculation, and respiratory disorder.

Further uses include the prevention and treatment of diseases or conditions associated with mitochondrial dysfunction. Mitochondria, central to metabolic processes, are involved with energy production, programmed cell death, and reactive oxygen species (ROS) generation. Traditionally, mitochondria have been considered as "end-function" organelles, receiving and processing vast amounts of cellular signals to regulate energy production and cell death. The peptides and pharmaceutical formulations thereof can be used to treat various age-related disease with much metabolic implications. Also they have an impact on has also been tested in various ways in vitro and in vivo to affect mitochondrial respiration, glucose transport, glucose utilization, glycolysis, insulin regulation and cellular proliferation/survival. Mitochondrial dysfunction is associated with but not limited to metabolic disorders, neurodegenerative diseases, chronic inflammatory diseases, and diseases of aging. Some mitochondrial diseases are due to mutations or deletions in the mitochondrial genome. Mitochondria divide and proliferate with a faster turnover rate than their host cells, and their replication is under control of the nuclear genome. If a threshold proportion of mitochondria in a cell is defective, and if a threshold proportion of such cells within a tissue have defective mitochondria, symptoms of tissue or organ dysfunction can result. Practically any tissue can be affected, and a large variety of symptoms may be present, depending on the extent to which different tissues are involved. In addition to congenital disorders involving inherited defective mitochondria, acquired mitochondrial dysfunction contributes to diseases, particularly neurodegenerative disorders associated with aging like Parkinson's, Alzheimer's, and Huntington's Diseases. The incidence of somatic mutations in mitochondrial DNA rises exponentially with age; diminished respiratory chain activity is found universally in aging people. Mitochondrial dysfunction is also implicated in excitotoxic neuronal injury, such as that associated with seizures or ischemia. Other disorders associated with mitochondrial dysfunction include chronic inflammatory disorders and metabolic disorders.

In addition, the formulations may be used for the disorders related to insulin receptor modulation including hypoglycemia, hyperinsulinemia, schizophrenia, fronto-temporal dementia, Guillain-Barré syndrome, Charcot-Marie-Tooth syndrome, insulin receptor impairment, Cushing's disease, Donohue syndrome, haemochromatosis, HIV infection, hyperglycemia, elevated blood levels of fatty acids or glycerol, hypertriglyceridemia, cephalic pain, glucagonomas, secretory disorders of the airway, osteoporosis, restenosis, renal failure, congestive heart failure, pulmonary edema, irritable bowel syndrome, acute coronary syndrome, post-surgical catabolic changes, hibernating myocardium, insufficient urinary sodium excretion, excessive urinary potassium concentration, respiratory distress, diarrhea, postoperative dumping syndrome, critical illness polyneuropathy (CIPN), organ tissue injury caused by reperfusion of blood flow following ischemia, and coronary heart disease risk factor (CHDRF) syndrome, peripheral vascular disease, diabetic neuropathy, glomerulonephritis, glomerulosclerosis, nephrotic syndrome, hypertensive nephrosclerosis, gallstones, cholescystitis, cholelithiasis, bone healing or regeneration, diseases of the eye and diabetic foot ulcers.

The peptide formulation of the present disclosure can be provided in accordance with one embodiment as part of a kit. Accordingly, in some embodiments, a kit for administering a peptide to a patient in need thereof is provided wherein the kit comprises a peptide formulation as described herein.

In one embodiment the kit is provided with a device for administering the composition to a patient, e.g., syringe needle, pen device, jet injector or another needle-free injector. The kit may alternatively or in addition include one or more containers, e.g., vials, tubes, bottles, infusion bag, single or multi-chambered pre-filled syringes, cartridges, infusion pumps (external or implantable), jet injectors, pre-filled pen devices and the like, optionally containing the peptide in a lyophilized form or in an aqueous solution. The kits in some embodiments comprise instructions for use. In accordance with one embodiment the device of the kit is an aerosol dispensing device, wherein the composition is prepackaged within the aerosol device. In another embodiment the kit comprises a syringe and a needle, and in one embodiment the sterile composition is prepackaged within the syringe.

In exemplary embodiments, the prefilled syringe or pen device may contain the formulation either in lyophilized form (which has then to be solubilized, e.g., with water for injection, prior to administration), or in aqueous form. Said syringe or pen device is often a disposable article for single use only, and may have a volume between 0.1 and 20 ml. However, the syringe or pen device may also be a multi-use or multi-dose syringe or pen. Said vial may also contain the formulation in lyophilized form or in aqueous form, and may serve as a single or multiple use device. As a multiple use device, said vial can have a bigger volume. Said infusion bag usually contains the formulation in aqueous form and may have a volume between 20 and 5000 ml.

The pharmaceutical formulations are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous injection, intraperitoneal injection, intramuscular injection, intrasternal injection, intravenous injection, intraarterial injection, intrathecal injection, intraventricular injection, intraurethral injection, intracranial injection, intrasynovial injection or infusions; or kidney dialytic infusion techniques.

In various embodiments, the peptide pharmaceutical composition can be systemically administered to the subject orally or via intravenous injection, intramuscular injection, subcutaneous injection, intraperitoneal injection, intraocular injection, intravitreal injection (e.g., injection into the vitreous humor), transdermal injection, intra-arterial injection, intrasternal injection, intrathecal injection, intraventricular injection, intraurethral injection, intracranial injection, intrasynovial injection or via infusions. In various embodiments, the pharmaceutical composition can be systemically administered to the subject via intramuscular injection, subcutaneous injection, transdermal injection, intrasternal injection, intraurethral injection, intracranial injection or intrasynovial injection. The pharmaceutical composition preferably contains at least one component that is not found in nature.

Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

The present disclosure includes compositions and methods for transdermal or topical delivery, to act locally at the point of application, or to act systemically once entering the body's blood circulation. In these systems, delivery may be achieved by techniques such as direct topical application of a substance or drug in the form of an ointment or the like, or by adhesion of a patch with a reservoir or the like that holds the drug (or other substance) and releases it to the skin in a time-controlled fashion. Preparations can include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, organic esters such as ethyl oleate, or fixed oils including synthetic mono or di-glycerides. Aqueous solvents include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like.

For example, in one embodiment, sterile injectable solutions can be prepared by incorporating a peptide in the required amount in an appropriate solvent with one or a combination of ingredients enumerated above, as required, followed by filtered sterilization. Generally, dispersions are prepared by incorporating the active peptide into a sterile vehicle that contains a basic dispersion medium and the required other ingredients from those enumerated above. In the case of sterile powders for the preparation of sterile injectable solutions, methods of preparation such as vacuum drying and freeze-drying yield a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin. In various embodiments, the injectable compositions will be administered using commercially available disposable injectable devices.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind known in the art. Injectable formulations are in accordance with the disclosure. The requirements for effective pharmaceutical excipients for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

Additionally, the peptide formulations of the present disclosures can be made into suppositories for rectal administration by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

The following examples are given merely to illustrate the present invention and not in any way to limit its scope. Before describing the experiments and their results in detail, it is mentioned that the said experiments were made with pharmaceutical formulations in which the active ingredient was a MOTS-c analog peptide. Due to the structural similarity of peptides sharing the concept, the skilled person will understand that the results obtained herein can be directly transferred to pharmaceutical formulations comprising similar peptides.

EXAMPLES

Example 1—Solubility Screening

A peptide, RWQEMNYIFYPR (SEQ ID NO: 10), acetate salt, was evaluated with a mix of standard formulations and concentrations. Formulations with 12.5 mg/mL peptide concentrations were prepared by serial dilution from 40 mg/mL. The components are described in Table 1.

TABLE 1

| No | Buffer | Tonicity Modifier | Solvent |
|---|---|---|---|
| 1 | N/A | N/A | 10% Polysorbate80 |
| 2 | N/A | N/A | 0.75% Isoleucine |
| 3 | N/A | N/A | 1 mM MgCl$_2$ |
| 4 | N/A | N/A | 2.5% 2-Hydroxypropyl-beta-cyclodextrin |
| 5 | 100 mM Acetate | N/A | N/A |
| 6 | 10 mM Acetate | 10% Sorbitol | N/A |
| 7 | N/A | N/A | 30% Ethanol |
| 8 | N/A | N/A | 60% PEG |
| 9 | N/A | N/A | 0.1% SDS |
| 10 | N/A | N/A | 2% Arginine |

The mix of standard formulations and concentrations were tested for stability at various peptide concentrations and storage temperatures. The results are included in Table 2. Results with asterisk indicate samples were incubated for more than 16 hr prior to status checking. All the formulations either precipitated or gelled within 24 hrs, especially at higher concentrations. However, five options were selected for further testing.

TABLE 2

| No. | Pep. Conc. mg/mL | Storage Temp | Observations |
|---|---|---|---|
| 1 | 12.5 | 25° C. | Slightly cloudy after 4.5 hr, gelled ≤ 24 hr |
|  | 40 |  | Gelled after 2.3 hr |
|  | 60 |  | Gelled after 3 hr |
|  | 12.5 | 40° C. | Cloudy at 50 min, gelled ≤ 24 hr |
|  | 40 |  | Gelled after 20 min |
|  | 60 |  | Gelled after 20 min |
| 2 | 12.5 | 25° C. | Gelled ≤ 24 hr |
|  | 40 |  | * Gelled ≤ 24 hr |
|  | 60 |  | * Gelled ≤ 24 hr |
|  | 12.5 | 40° C. | Gelled ≤ 20 min |
|  | 40 |  | Gelled ≤ 20 min |
|  | 60 |  | Gelled ≤ 20 min |
| 3 | 12.5 | 25° C. | Cloudy, gelled after 1.5 hr |
|  | 40 |  | Cloudy, viscous, gelled after 1.5 hr |
|  | 12.5 | 40° C. | Gelled after 1.5 hr |
|  | 40 |  | Gelled after 1.5 hr |

TABLE 2-continued

| No. | Pep. Conc. mg/mL | Storage Temp | Observations |
|---|---|---|---|
| 4 | 12.5 | 25° C. | * Gelled ≤ 24 hr |
|  | 40 |  | * Gelled ≤ 24 hr |
|  | 60 |  | * Gelled ≤ 24 hr |
|  | 12.5 | 40° C. | * Gelled ≤ 24 hr |
|  | 40 |  | * Gelled ≤ 24 hr |
|  | 60 |  | * Gelled ≤ 24 hr |
| 5 | 12.5 | 25° C. | * Gelled ≤ 24 hr |
|  | 40 |  | * Gelled ≤ 24 hr |
|  | 12.5 | 40° C. | * Gelled ≤ 24 hr |
|  | 40 |  | * Gelled ≤ 24 hr |
| 6 | 12.5 | 25° C. | * Gelled ≤ 24 hr |
|  | 40 |  | * Gelled ≤ 24 hr |
|  | 12.5 | 40° C. | * Gelled ≤ 24hr |
|  | 40 |  | * Gelled ≤ 24 hr |
| 7 | 40 | 25° C. | Gelled immediately |
|  | 40 | 40° C. | Gelled immediately |
| 8 | 40 | 25° C. | Gelled immediately |
|  | 40 | 40° C. | Gelled immediately |
| 9 | 40 | 25° C. | Precipitated |
|  | 40 | 40° C. | Precipitated |
| 10 | 40 | 25° C. | Precipitated |
|  | 40 | 40° C. | Precipitated |

Example 2

Components 1, 2, 4, 5 and 6 were selected for further testing. It was hypothesized that the gel formation at higher peptide concentrations generated potential nucleation sites that persisted during dilution to lower concentrations and induced gel formation in the lower concentration formulations. To reduce the likelihood of gel formation, the different formulation concentrations of the $2^{nd}$ screen (5 mg/ml. 12.5 mg/ml and 20 mg/ml) were prepared individually (not by serial dilution). The formulations are described in Table 3 and the results are provided in Table 4.

TABLE 3

| No | Buffer | Tonicity Modifier | Solvent |
|---|---|---|---|
| 1 | N/A | N/A | 10% Polysorbate 80 |
| 2 | N/A | N/A | 0.75% Isoleucine |
| 4 | N/A | N/A | 2.5% 2-Hydroxypropyl-betacyclodextrin |
| 5 | 100 mM Acetate | N/A | N/A |
| 6 | 10 mM Acetate | 10% Sorbitol | N/A |

TABLE 4

| No. | Peptide Conc. mg/mL | Storage Temp | Observations |
|---|---|---|---|
| 1 | 5 | 5° C. | Clear liquid at 6 days |
|  | 12.5 |  | Clear liquid at 6 days |
|  | 20 |  | Clear liquid at 6 days |
|  | 5 | 25° C. | Clear liquid at 6 days |
|  | 12.5 |  | Cloudy liquid at 6 days |
|  | 20 |  | Cloudy, white gel ≤ 21 hours |
|  | 5 | 40° C. | Cloudy liquid at 6 days |
|  | 12.5 |  | Semi-gelled ≤ 6 days |
|  | 20 |  | Cloudy, white gel ≤ 1 hour |
| 2 | 5 | 5° C. | Clear liquid at 6 days |
|  | 12.5 |  | Clear liquid at 6 days |
|  | 20 |  | Clear liquid at 6 days |
|  | 5 | 25° C. | Cloudy, white gel ≤ 21 hours |
|  | 12.5 |  | Cloudy, white gel ≤ 1.5 hours |
|  | 20 |  | Clear gel ≤ 1.5 hours |
|  | 5 | 40° C. | Semi-gelled ≤ 6 days |
|  | 12.5 |  | Cloudy, white gel ≤ 1 hour |
|  | 20 |  | Cloudy, white gel ≤ 30 minutes |
| 4 | 5 | 5° C. | Clear liquid at 6 days |
|  | 12.5 |  | Clear liquid at 6 days |
|  | 20 |  | Clear liquid at 6 days |
|  | 5 | 25° C. | Cloudy, white gel ≤ 5 days |
|  | 12.5 |  | Cloudy, white gel ≤ 21 hours |
|  | 20 |  | Clear gel ≤ 2 hours |
|  | 5 | 40° C. | Semi-gelled ≤ 6 days |
|  | 12.5 |  | Cloudy, white gel with fibers ≤ 21 hours |
|  | 20 |  | Cloudy, white gel ≤ 1 hour |
| 5 | 5 | 5° C. | Clear liquid at 6 days |
|  | 12.5 |  | Clear liquid at 6 days |
|  | 20 |  | Clear liquid at 6 days |
|  | 5 | 25° C. | Clear liquid at 6 days |
|  | 12.5 |  | Cloudy, white gel ≤ 5 days |
|  | 20 |  | Cloudy, white gel ≤ 21 hours |
|  | 5 | 40° C. | Semi-gelled ≤ 48 hrs; Clear liquid at 6 days |
|  | 12.5 |  | Cloudy, white gel ≤ 21 hours |
|  | 20 |  | Cloudy, white gel ≤ 4 hours |
| 6 | 5 | 5° C. | Clear liquid at 6 days |
|  | 12.5 |  | Clear liquid at 6 days |
|  | 20 |  | Clear liquid at 6 days |
|  | 5 | 25° C. | Clear liquid at 6 days |
|  | 12.5 |  | Clear liquid at 6 days |
|  | 20 |  | Clear liquid at 6 days |
|  | 5 | 40° C. | Clear liquid at 6 days |
|  | 12.5 |  | Clear liquid at 6 days |
|  | 20 |  | Clear gel at 46 hours |

Example 3

Further formulations were prepared as described in Table 5. The peptide concentrations (RWQEMNYIFYPR (SEQ ID NO: 10) acetate salt, 12.5 and 25 mg/ml) were prepared individually (not by serial dilution). The results are reported in Table 6.

TABLE 5

| No | Buffer | Tonicity Modifier | Solvent |
|---|---|---|---|
| 11 | 100 mM L-glycine | N/A | N/A |
| 12 | N/A | N/A | 10% Glycerol |
| 13 | N/A | N/A | 10% PEG |

TABLE 6

| No. | Peptide. Conc. mg/mL | Storage Temp | Observations |
|---|---|---|---|
| 11 | 12.5 | 25° C. | Gelled ≤ 90 min |
|  | 25 |  | Gelled ≤ 90 min |
| 12 | 12.5 | 25° C. | Gelled ≤ 90 min |
|  | 25 |  | Gelled ≤ 90 min |
| 13 | 12.5 | 25° C. | Gelled ≤ 90 min |
|  | 25 |  | Gelled ≤ 90 min |

Example 4

Glutamic acid containing formulations were prepared as described in Table 7. The peptide concentrations (RWQEMNYIFYPR (SEQ ID NO: 10) acetate salt, 12.5 and 25 mg/ml) where the prepared individually (not by serial dilution). The results are reported in Table 8. 50 mM glutamic acid was an effective solubilizer for the peptide. All the other liquid formulations precipitated or gelled within 24 hours at room temperature, especially at higher concentrations (40 mg/mL). The peptide in 50 mM glutamic acid at 50 mg/mL remains stable for 6 days at room temperature. This solubilizer was lyophilized to evaluate high concentration (≥50 mg/mL) feasibility.

TABLE 7

| No | Buffer | Tonicity Modifier | Solvent |
|---|---|---|---|
| 14 | N/A | N/A | 50 mM Glutamic Acid |
| 15 | 10 mM Histidine | N/A | 50 mM Glutamic Acid |

TABLE 8

| No. | Peptide Conc. mg/mL | Storage Temp | Observations |
|---|---|---|---|
| 14 | 5 | 5° C. | Clear liquid |
|  | 50 |  | Cloudy liquid ≤ 6 days |
|  | 5 | 25° C. | Clear liquid ≤ 6 days |
|  | 50 |  | Cloudy liquid ≤ 4 days; viscous liquid ≥ 4 days; Cloudy gel ≤ 6 days |
|  | 5 | 40° C. | Clear liquid ≤ 6 days |
|  | 50 |  | Viscous liquid < 24 hours; cloudy, viscous liquid ≥ 24 hours; Cloudy gel ≤ 4 days |
| 15 | 5 | 5° C. | Clear liquid ≤ 6 days |
|  | 5 | 25° C. | Clear liquid ≤ 6 days |
|  | 5 | 40° C. | Clear liquid ≤ 6 days |

Example 5

Glutamic acid containing formulations of RWQEMNYIFYPR (SEQ ID NO: 10) acetate salt, were tested as described in Table 9. Glutamic acid solutions were prepared in water at 50 mM (pH=3) with vortexing and warming at 37° C. The peptide concentrations (12.5 and 25 mg/ml) were prepared individually. Formulations were prepared in ~1 ml (dependent on actual peptide amount) in 15 ml conical tubes, then transfer 900 μL to 1.7 ml microfuge tubes. The formulation with 25 mg/ml in ~50 mM L-glutamic acid were pH 4; the formulation with 12.5 mg/ml peptide in ~50 mM L-glutamic acid were pH 3.5. After 74 h, both samples were still clear with no change in viscosity, appear normal.

TABLE 9

| Excipient | Peptide Conc. | Initial Appearance | Observations |
|---|---|---|---|
| L-glutamic acid ~50 mM | 25 mg/ml | clear | 6 d: still clear/normal |
|  | 12.5 mg/ml | clear | 6 d: still clear/normal |

Example 6

Further Glutamic acid containing formulations of RWQEMNYIFYPR (SEQ ID NO: 10) acetate salt were tested as described in Tables 10-11. Glutamic acid solutions were prepared in water at ~50 mM, and diluted to ~25 mM, and ~10 mM with vortexing and warming at 37° C. All three solutions were pH 3. The peptide concentrations (10, 50 and 100 mg/ml) were prepared individually. Formulations were prepared in ~1 ml (dependent on actual peptide amount) in 15 ml conical tubes, then transfer 900 μL to 1.7 ml microfuge tubes. Gels that formed at ~10 mM L-glutamic acid were more opaque than 25 mM L-glutamic acid, which was cloudier than 50 mM L-glutamic acid. *100 mg/ml peptide in ~10 mM glutamic acid was very cloudy at 20 min but appeared not homogenous. At 1h the sample was clear again with no sign of viscosity increase.

TABLE 10

| Excipient | Peptide Conc. | Initial Appearance | Observations |
|---|---|---|---|
| L-glutamic acid ~50 mM | 100 mg/ml | clear | 19.5 h: clear but extremely viscous, nearly solid gel 22 h: gel/clear |
|  | 50 mg/ml | clear | 19.5 h: clear/normal 72 h: clear but may be slight increase in viscosity |
|  | 25 mg/ml | clear | 19.5 h: clear/normal 72 h: clear/normal |
| L-glutamic acid ~25 mM | 100 mg/ml | clear | 19.5 h: clear but very viscous, slightly better than 50 mM L-GA 22 h: extremely viscous, nearly solid gel/clear 26 h: very viscous/clear, still not solid gel 44 h: gel, does not appear homogenous |
|  | 50 mg/ml | clear | 19.5 h: clear/normal 48 h: clear/normal 72 h: clear but may be slight increase in viscosity |
|  | 25 mg/ml | clear | 19.5 h: clear/normal 72 h: clear/normal |
| L-glutamic acid ~10 mM | 100 mg/ml | clear | 20 min: very cloudy but not homogenous 2.5 h: cloudy, homogenous 19.5 h: gel |
|  | 50 mg/ml | clear | 2.5 h: slightly cloudy but not homogenous 19.5 h: gel |
|  | 25 mg/ml | clear | 19.5 h: extremely viscous, nearly solid gel/cloudy 22 h: gel |

TABLE 11

| Excipient | Peptide mg/ml | Initial | Comments |
|---|---|---|---|
| L-glutamic acid ~50 mM | 100 | clear | 22 h: gel/clear |
|  | 50 | clear | 48 h: clear/normal 92 h: clear but slight increase in viscosity |
|  | 25 | clear | 74 h: clear/normal 92 h: clear/normal |
| L-glutamic acid ~25 mM | 100 | clear | >26 h (44 h): gel, does not appear homogenous |
|  | 50 | clear | 48 h: clear/ normal 74 h: slight haze and increase in viscosity, more so than 50 mM 92 h: viscous//cloudy |
|  | 25 | clear | 74 h: clear/normal 92 h: clear/normal |
| L-glutamic acid ~10 mM | 100 | clear | 20 min: very cloudy, not homogenous 19.5 h: gel |
|  | 50 | clear | 2.5 h: slightly cloudy 19.5 h: gel |
|  | 25 | clear | 22 h: gel |

Example 7

Solution formulations were prepared comprising 50 mg/mL of the peptide of SEQ ID NO: 10 in water with 50 mM L-glutamic acid and either 2.5% sorbitol or no tonicity modifier. Solution formulations were mixed to dissolve, sterilized by filtration through 0.2 μm membrane filters, filled at a 0.75 mL volume into 3 cc sterilized glass vials, stoppered, capped, labeled, and stored at controlled conditions (−70° C./ambient relative humidity, −20° C./ambient relative humidity, 5° C./ambient relative humidity, 25° C./60% relative humidity, or 40° C./75% relative humidity) or were lyophilized before capping and storage at the same conditions.

Samples of both liquid and lyophilized (reconstituted in water) formulations were tested at time zero and additional samples were removed from storage at intervals over 12 weeks and assessed for stability. Initial properties and stability after storage were both assessed by a combination of methods comprising appearance, pH, concentration determined by UV absorbance, purity determined by HPLC, turbidity determined by optical density between 300 nM and 700 nM, and particulate content using by FlowCAM particle imaging system. Solution formulations (thawed as necessary for analysis) showed good stability for at least 1 week at 25° C./60% relative humidity and for at least 12 weeks at −70° C./ambient relative humidity and −20° C./ambient relative humidity. All samples tested at these time points were colorless solutions free of visible particles, with concentrations at or near their target values. At 12 weeks, liquid formulations stored at −70° C./ambient relative humidity and −20° C./ambient relative humidity were stable in terms of purity, showing main HPLC peak percentages ranging from 97.9%-98.0%, comparable to the initial values (97.0%-97.9%).

Lyophilized formulations showed good stability at 5° C./ambient relative humidity and 25° C./60% relative humidity for at least 12 weeks. At 12 weeks, lyophilized formulations were colorless and free of visible particles upon reconstitution. Lyophilized formulations stored at all conditions were stable in terms of purity, showing main HPLC peak percentages ranging from 96.9%-98.1% by HPLC, comparable to initial values (97.7%-97.9%).

Example 8—Biological Exposure Assay of Formulation

Solution formulations were prepared comprising 50 mg/mL of the peptide of SEQ ID NO: 10 in water with 50 mM L-glutamic acid and either 2.5% sorbitol or no tonicity modifier. The formulations were stored frozen until administered to male cynomolgus monkeys (3 animals per treatment group) as a single dose of 25 mg/kg of the peptide of SEQ ID NO: 10 by subcutaneous injection. An additional group of 3 male cynomolgus monkeys received a single subcutaneous 25 mg/kg dose of an aqueous solution of the peptide of SEQ ID NO: 10 (50 mg/mL) prepared immediately prior to dosing and administered before gelling occurred. Whole blood samples were collected from all animals at intervals over 12 hours and quenched by addition of a solution containing acetonitrile/methanol (3:1) and 0.1% Triton X-100. Quenched blood samples were frozen and stored at −70° C. until analyzed.

Quenched blood samples were analyzed for concentrations of the peptide of SEQ ID NO: 10 using a sensitive and specific LC/MS-MS method. Maximum concentrations of the peptide in whole blood (Cmax) were 10.8 ng/mL for the aqueous solution formulation without L-glutamic acid, 12.0 ng/mL for the solution formulation with 50 mM L-glutamic acid, and 32.1 ng/mL for the solution formulation with 50 mM L-glutamic acid and 2.5% sorbitol. Therefore, the addition of the stabilizer L-glutamic acid to the peptide formulation did not impede the absorption of the peptide following subcutaneous administration.

Example 9

Solution formulations are prepared comprising 50 mg/mL of the peptide of SEQ ID NO: 10 in water with 50 mM L-glutamic acid and either 2.5% sorbitol or no tonicity modifier. Solution formulations are mixed to dissolve. Drug substance is added and mixed to dissolve. The resulting solution is filtered through 0.2 μm membrane filters. The solution is lyophilized or stored as a solution. Following subcutaneous injection of the solution, the release of the drug substance is sustained over an extended period of time relative to administration of drug substance alone.

All of the articles and methods disclosed and claimed herein can be made and executed without undue experimentation in light of the present disclosure. While the articles and methods of this disclosure have been described in terms of preferred embodiments, it will be apparent to those of skill in the art that variations may be applied to the articles and methods without departing from the spirit and scope of the disclosure. All such variations and equivalents apparent to those skilled in the art, whether now existing or later developed, are deemed to be within the spirit and scope of the disclosure as defined by the appended claims. For example, all aspects and/or embodiments described herein as methods of using are also contemplated as a composition for use as described, or a composition for use in a medicament for the specified use. All patents, patent applications, and publications mentioned in the specification are indicative of the levels of those of ordinary skill in the art to which the disclosure pertains. The disclosure illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law). All headings and sub-headings are used herein for convenience only and should not be construed as being limiting in any way. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure. The citation and incorporation of patent documents herein is done for convenience only and does not reflect any view of the validity, patentability, and/or enforceability of such patent documents.

This disclosure includes all modifications and equivalents of the subject matter recited in the aspects appended hereto as permitted by applicable law.

What is claimed is:

1. A formulation comprising a peptide, or a pharmaceutically acceptable salt thereof, and glutamic acid or a salt thereof,
wherein the peptide comprises the amino acid sequence RWQEMNYIFYPR (SEQ ID NO: 10),
wherein the peptide, or the pharmaceutically acceptable salt thereof, is present in the formulation at a concentration in the range from about 5 mg/ml to about 100 mg/ml,
wherein the glutamic acid concentration is in the range from about 15 mM to about 100 mM, and
wherein the formulation has a pH of 3 to about 4.

2. The formulation of claim 1, wherein the formulation is in liquid form.

3. The formulation of claim 1, wherein the glutamic acid concentration is in the range from about 25 mM to about 100 mM.

4. The formulation of claim 1, wherein the glutamic acid concentration is about 25 mM.

5. The formulation of claim 1, wherein the peptide, or the pharmaceutically acceptable salt thereof, is present in the formulation at a concentration in the range from about 10 mg/ml to about 50 mg/ml.

6. The formulation of claim 5, wherein the concentration of the peptide, or the pharmaceutically acceptable salt thereof, is about 25 mg/ml.

7. The formulation of claim 1, wherein the composition comprises the peptide salt RWQEMNYIFYPR acetate (SEQ ID NO: 10).

8. The formulation of claim 1, further comprising sorbitol.

9. A prefilled syringe or pen, a vial or an infusion bag, said syringe or pen, vial or infusion bag containing the formulation of claim 1.

10. A formulation according to claim 1 that has been freeze-dried.

11. A method of making formulation of claim 1, the method comprising mixing a peptide or a pharmaceutically acceptable salt thereof with an aqueous solution of glutamic acid, or a salt thereof, in amounts effective to create a formulation comprising the peptide or salt thereof at a concentration of 5 mg/ml to 100 mg/ml and the glutamic acid or salt thereof at a concentration of 15 mM to 100 mM, and having a pH of 3 to 4, wherein the peptide comprises the amino acid sequence of RWQEMNYIFYPR (SEQ ID NO: 10).

12. The formulation of claim 1, wherein the peptide concentration is about 12.5 mg/mL.

13. The formulation of claim 1, wherein the formulation is aqueous.

14. The formulation of claim 1 that has a pH of 3.5.

15. The formulation of claim 1 that has a pH of about 4.

* * * * *